United States Patent
Amano et al.

[11] Patent Number: 6,081,742
[45] Date of Patent: Jun. 27, 2000

[54] ORGANISM STATE MEASURING DEVICE AND RELAXATION INSTRUCTING DEVICE

[75] Inventors: Kazuhiko Amano, Suwa; Kazuo Uebaba, Yokohama; Hitoshi Ishiyama, Toride, all of Japan

[73] Assignee: Seiko Epson Corporation, Tokyo, Japan

[21] Appl. No.: 09/068,755

[22] PCT Filed: Sep. 4, 1997

[86] PCT No.: PCT/JP97/03108

§ 371 Date: Aug. 4, 1998

§ 102(e) Date: Aug. 4, 1998

[87] PCT Pub. No.: WO98/10699

PCT Pub. Date: Mar. 19, 1998

[30] Foreign Application Priority Data

Sep. 10, 1996 [JP] Japan ................................. 8-239608

[51] Int. Cl.$^7$ ...................................................... A61B 5/04
[52] U.S. Cl. ............................................ 600/513; 600/484
[58] Field of Search .................................. 600/483, 484, 600/513

[56] References Cited

U.S. PATENT DOCUMENTS

| | | |
|---|---|---|
| 4,805,629 | 2/1989 | Farges . |
| 5,360,008 | 11/1994 | Campbell, Jr. ............................ 600/484 |
| 5,759,156 | 6/1998 | Hayakawa et al. . |
| 5,776,070 | 7/1998 | Kitazawa et al. ...................... 600/483 |
| 5,830,148 | 11/1998 | Inukai et al. . |

FOREIGN PATENT DOCUMENTS

| | | |
|---|---|---|
| 0 645 117 | 3/1995 | European Pat. Off. . |
| 0 659 384 | 6/1995 | European Pat. Off. . |
| 2341948 | 3/1973 | Germany . |
| 49-65084 | 6/1974 | Japan . |
| 52-39983 | 3/1977 | Japan . |
| 62-22627 | 1/1987 | Japan . |
| 4-51912 | 5/1992 | Japan . |
| 4-136207 | 12/1992 | Japan . |
| 4-348761 | 12/1992 | Japan . |
| 5-37420 | 2/1993 | Japan . |
| 5-76501 | 3/1993 | Japan . |
| 5-200001 | 8/1993 | Japan . |
| 5-200004 | 8/1993 | Japan . |
| 6-142082 | 5/1994 | Japan . |
| 6-22325 | 6/1994 | Japan . |
| 7-88092 | 4/1995 | Japan . |
| 60-109633 | 7/1995 | Japan . |
| 6-227383 | 8/1995 | Japan . |
| 2 258 149 | 2/1993 | United Kingdom . |
| 2 259 772 | 3/1993 | United Kingdom . |

*Primary Examiner*—William E. Kamm
*Assistant Examiner*—Carl H. Layno
*Attorney, Agent, or Firm*—Eric B. Janofsky

[57] ABSTRACT

Devices are known for measuring a subject's respiratory rate based on the subject's pulse wave or level of electrocardiogram. When the subject is exercising or carrying out daily activities, however, an electromyogram becomes imposed on the cardiogram waveform, so that a body motion component is superimposed on the pulse wave. This leads to an incorrect measured result. To overcome this drawback, a portable portion in the form of a wristwatch worn by the subject and a personal computer comprising device main body 330 are provided. A photoelectric pulse wave sensor is attached to the base of the subject's finger, and the pulse waveform is measured. An acceleration sensor is provided to the portable portion, and employed to detect the subject's body motion spectrum. Device main body 330 performs a window function on the pulse wave, and removes the acceleration component, so that the body motion spectrum is removed from the frequency spectrum of the pulse wave. Using the obtained result, the respiratory rate and change rate of the respiratory rate are generated.

18 Claims, 24 Drawing Sheets

| PEAK ADDRESS ADR3 | 0 | 1 | 2 | 3 | 4 |
|---|---|---|---|---|---|
| WAVEFORM VALUE ADDRESS ADR1 | | | | | |
| PEAK TYPE B/T | | | | | |
| WAVEFORM VALUE W | | | | | |
| STROKE STRK | | | | | |
| SLOPE INFORMATION SLP | | | | | |

PEAK INFORMATION {

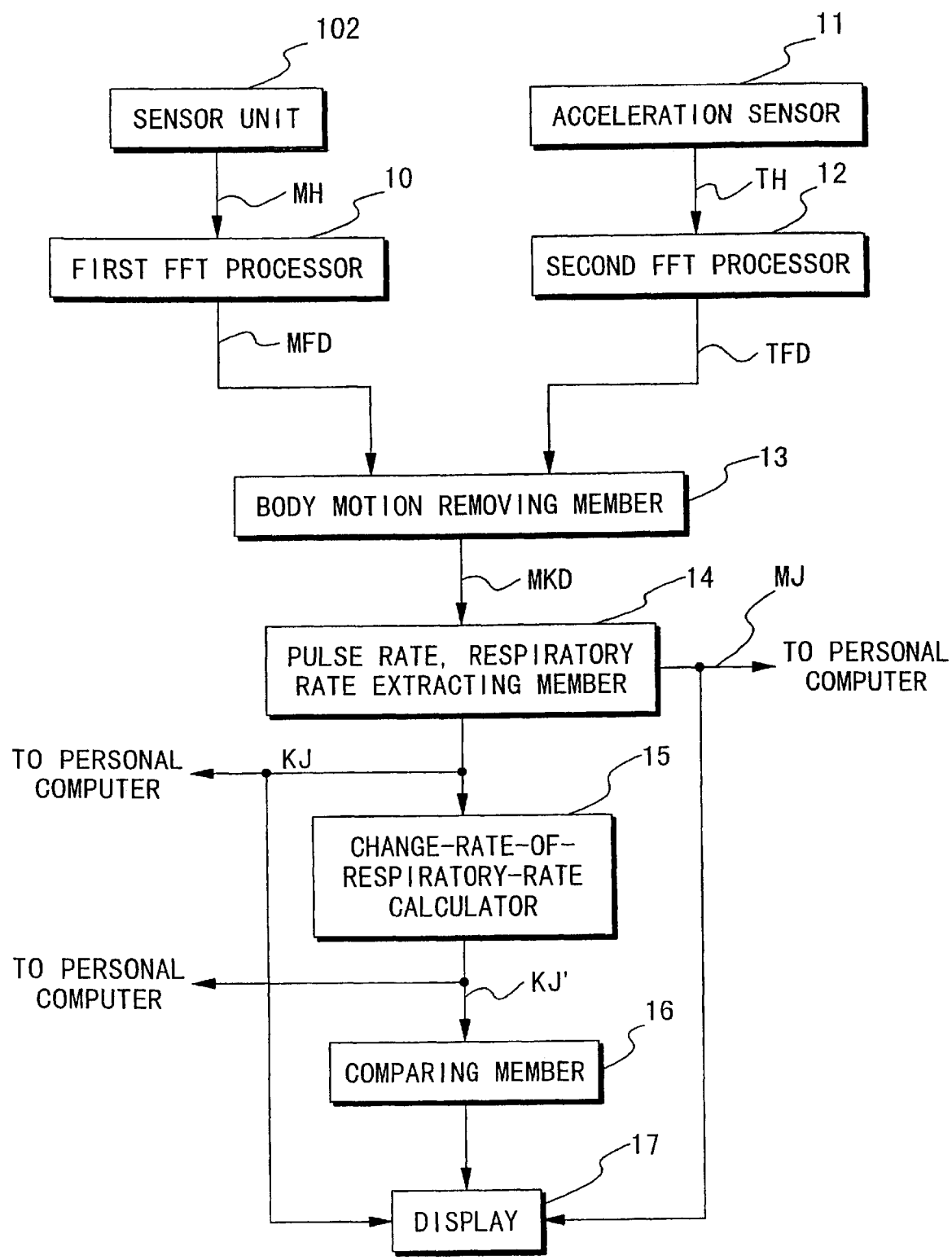

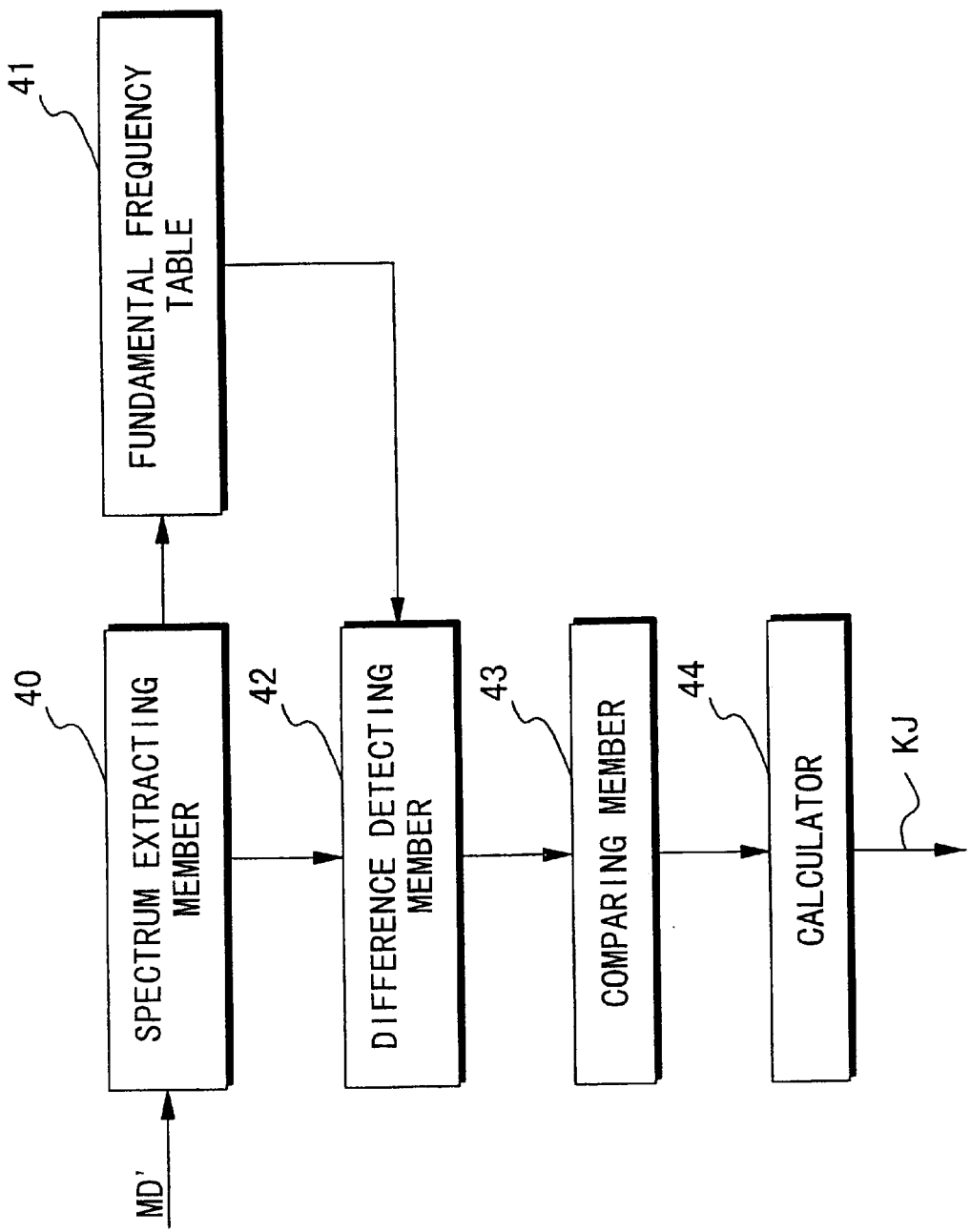

ORGANISM STATE MEASURING DEVICE AND RELAXATION INSTRUCTING DEVICE

TECHNICAL FIELD

The present invention relates to a physiological state measuring device suitable for monitoring health, and particularly measuring the respiratory rate, during exercise. The present invention also concerns a relaxation guidance device which determines a subject's degree of relaxation during meditation or exercise based on changes in the respiratory rate calculated by the aforementioned physiological state measuring device, and then guides the subject into a relaxed state by informing the subject of the result of the determination.

BACKGROUND OF THE INVENTION

It is well known that the relationship between pulse and respiratory rates may serve as an indicator of a subject's psychological or physical health. For example, in the case of illness, the pulse rate/respiratory rate ratio may increase or decrease.

The following is known about the relationship between the respiratory rate and the physiological state. Namely:
 (i) There is a large change rate of the respiratory rate when a subject is at rest
 (ii) The change rate of the respiratory rate becomes small when the subject performs exercise of moderate intensity
 (iii) During intense exercise, regular breathing becomes impossible and the change rate of the respiratory rate becomes large Autonomic training, also known as concentrated self-relaxation technique, is known to be helpful in promoting or restoring health by reducing tension. This type of training emphasizes placing the mind in a state of relaxation. However, the subject may become too focused on his efforts to relax, so that tension results instead. Breathing exercise has been developed as a part of autonomic training, to aid the subject in easing tension and shifting into a state of relaxation. For example, the subject chants a phrase such as "breath slowly" to himself repeatedly. As a result, the subject is able to enter a state of relaxation.

Various Eastern meditation and health methods emphasize breathing manner. For example, regularity of breathing in very important in Zen meditation which teaches the subject to regulate "the body, breathing and mind." Similarly, breathing exercise is one of the eight training steps in yoga. In addition, meditation employs abdominal breathing. These Eastern breathing methods share the common feature of training the subject to conduct abdominal breathing, in order to accomplish mental relaxation.

The change rate of the respiratory rate is known to decrease when the mind has been placed in a relaxed such as described above.

Considerable medical attention has also been directed on respiration during sleep. As a result, it is now known that there is a high likelihood of sudden death in the presence of apnea syndromes. In Eastern medicine, the heart rate of a healthy subject is viewed to be four times of his respiratory rate. A heart rate which is less than this is referred to as a slow pulse, while a heart rate which is greater than this is called a fast pulse. In these cases, it is very likely that the subject suffers from some sort of physiological illness. In other words, the respiration pulse rate ratio may become indicator of health. Moreover, the present inventors discovered that this respiration pules rate relationship is maintained during exercise.

Namely, subjects with slow pulse frequently suffer from parasympathetic dominance, asthma, autonomic imbalances, hynoteneion, and so on. On the other hand, subjects with fast pulse frequently suffer from high blood pressure, pneumonia, hepatitis, or other inflammatory diseases. Accordingly, if data can be obtained for pulse and respiratory rates during daily activities, it is possible to estimate the subject's state of health. In recent years, however, there has also been an increasing need to detect a subject's physiological state not only during daily activities, but also when the subject is active or exercising (pulse rate, arrhythmia, respiratory rate, etc.), such as in the case of scientific training or health monitoring of an athlete.

How the respiratory rate is measured is an important problem. Typical method for measuring the respiratory rate in a sedentary subject, such as a sick patient, include applying a band around the subject's chest or stomach, and then counting the number of expansions and contractions, or inserting a thermocouple in the subject's nostrils and counting the variation in the resistance value. However, employing such devices in a subject who is monitoring his daily health, or who is carrying out training would provide a considerable inconvenience.

A frequency analysis RR interval fluctuation in an electrocardiogram at rest reveals the presence of a component corresponding to the respiratory rate. Since the pulse wave is synchronized with the electrocardiogram, a component corresponding to the respiratory rate should be also included in the frequency analysis of the fluctuation pattern of the pulse wave cycle (or the pulse wave amplitude).

A device has been disclosed which measures the respiratory rate based on an electrocardiogram or pulse wave, by extracting this component. For example, Japanese Patent Application Show 62-22627 discloses calculating the respiratory rate by measuring continuous pulse intervals, measuring the cycle of fluctuation in these pulse intervals, and then taking the reciprocal of the cycle of fluctuation.

JPUA 451912 discloses a technique in which a first respiratory rate is detected based on the fluctuation in the envelope formed by the peak values of the pulse waveform or the cycle of fluctuation in the RR interval in the waveform of the electrocardiac waveform, a second respiratory rate is detected by detecting the up-and-down motion of the surface of the subject's trunk, and recording and displaying the lower of these two respiratory rates.

JPUA 4136207 discloses estimating the respiratory rate based on the fluctuation cycle in the amplitude of the pulse waveform, and calculating the average value of the pulse waveform (the wave in the low frequency component). By employing data obtained during the average value trend is small, the influence from swell or noise can be reduced.

JPA 6142082 discloses multiplying a subject's maximum blood pressure value and pulse rate which are successively obtained, and then calculating the respiratory rate based on the pulse cycle of the multiplied value. JPUB 622325 discloses a technique for determining the respiratory rate based on the cycle of fluctuation of a curved line connecting peak values in the pulse wave.

Accordingly, the present inventors hypothesized that the relationships described above were maintained during exercise, i.e., that the respiratory rate could be estimated based on an electrocardiogram or pulse wave during exercise. Clinical studies were carried out to test this hypothesis. As a result, it was understood that a component corresponding to respiratory rate is present in the frequency component of the pulse wave fluctuation or the RR interval fluctuation of an electrocardiogram during exercise.

However, in the case of an exercising subject, an electromyogram is superimposed on the electrocardiogram waveform, while a body motion component gets superimposed on the pulse wave. Since these components have a higher level than the components corresponding to the respiratory rate, calculations were carried out using an incorrect respiratory rate based on components obtained during exercise.

The present invention was conceived in consideration of the above circumstances, and has its objective of the provision of a physiological state measuring device which can accurately and easily measure a subject's respiratory rate, particularly during exercise. It is another objective of the present invention to provide a device which extracts the respiratory component from the pulse wave, and then guides the subject based on the rate of change in the extracted component, so that the subject enters a relaxed mental state.

DISCLOSURE OF THE INVENTION

The present invention was conceived in view of the above-described circumstances. The invention according to claim 1 is characterized in the provision of a circulatory system information detecting means for detecting information about the subject's circulatory system; and an extracting means for extracting a region determined according to the pulse or heart rate from among the results of frequency analysis on the detected circulatory system information, and measuring the respiratory rate of the subject based on the extracted region.

The invention according to claim 2 is characterized in the provision of a circulatory system information detecting means for detecting information about the subject's circulatory system; an extracting means for extracting a region determined according to the pulse or heart rate from the among the frequency spectrums for the detected circulatory system information; and a measuring means for measuring the subject's respiratory rate based on the frequency spectrum in the extracted range.

The invention according to claim 3 is characterized in that the circulatory system information is the amount of change in the cycle of the pulse wave or the level of the electrocardiogram.

The invention according to claim 4 is characterized in that the circulatory system information is the amount of change in the amplitude value of the pulse wave or the level of the electrocardiogram.

The invention according to claim 5 is characterized in the provision of a portable portion which is attached to the subject for detecting the circulatory system information, and a main portion designed to enable communication with the portable portion.

The invention according to claim 6 is characterized in the provision of a body motion removing means for removing the body motion spectrum corresponding to the subject's body motion from the frequency spectrum extracted by the extracting means, wherein the subject's respiratory rate is generated based on the output from the body motion removing means.

The invention according to claim 7 is characterized in that the body motion removing means is provided with a body motion detecting means for detecting the subject's body motion; a body motion spectrum detecting means for determining the body motion spectrum corresponding to the subject's body motion, based on the results detected by the body motion detecting means; and a body motion correcting means for removing the body motion spectrum from the frequency spectrum extracted by the extracting means.

The invention according to claim 8 is characterized in that the body motion removing means is provided with a fundamental frequency table in which associations have been created in advance for the respiratory fundamental frequency and the body motion fundamental frequency according to the change in exercise intensity; and a frequency specifying member for referencing the fundamental frequency table and specifying the respiratory fundamental frequency and the body motion fundamental frequency from among the frequency spectrums extracted by the extracting means; wherein the respiratory rate is calculated based on the respiratory fundamental frequency specified by the frequency specifying member.

The invention according to claim 9 is characterized in that the body motion detecting means detects acceleration of the subject's arms, and the body motion correcting means removes the body motion spectrum corresponding to the frequency of the acceleration from the frequency spectrum.

The invention according to claim 10 is characterized in the provision of a warning means for providing a warning relying on the subject's five senses, when the measured respiratory rate is outside a specific range.

The invention according to claim 11 is characterized in the provision of a calculating means for calculating the change rate of the respiratory rate based on the measured respiratory rate.

The invention according to claim 12 is characterized in the provision of a communicating means for sending and receiving information including indicators of physiological state to and from an external device which is provided separately from the main body of the device.

The invention according to claim 13 is characterized in that the communicating means is provided with a recognition information recording means in which particular recognition numbers are provided, wherein a recognition number is associated with communicated information and sent between the external device and the device main body.

The invention according to claim 14 is characterized in that data transmission between the device main body and the external device is carried out using compressed data.

The invention according to claim 15 is a relaxation guidance device employing the aforementioned physiological state measuring device, characterized in the provision of an indicator generating means for generating indicators showing the subject's degree of relaxation based on the change rate of the respiratory rate calculated by the calculating means, and a notifying means for notifying the subject of the indicator.

The invention according to claim 16 is characterized in that the indicator generating means generates an indicator showing the subject's degree of relaxation based on a comparison between a threshold value and the change rate of the respiratory rate.

The invention according to claim 17 is characterized in that the indicator generating means is provided with a pulse rate calculating means for determining pulse rate based on circulatory system information, a rate-of-change-in-pulse-rate calculating means for calculating the rate of change in the pulse rate; and a threshold value table for storing in advance threshold values which have been associated with rates of change in the pulse rate; wherein the indicator generating means references the rate of change in the pulse rate calculated by the rate-of-change-in-pulse-rate calculating means, reads out the threshold values from the threshold value table, and generates indicators showing the subject's degree of relaxation based on the threshold value.

The invention according to claim 18 is provided with a communicating means which sends the change rate of the respiratory rate calculated by the calculating means, and receives the indicator generated by the indicator generating means which is provided to the external device, to and from the external device which is provided external to the main body of the device, wherein the subject is notified of the indicator by the notifying means provided to the device main body.

BRIEF DESCRIPTION OF THE FIGURES

FIG. 21 is a block diagram showing the functional structure of the first embodiment.

FIG. 25($b$) shows analysis data MD' from which the pulse wave component has been removed.

FIG. 26 is a block diagram showing the detailed functional structure of respiratory rate extracting member 22.

DESCRIPTION OF THE PREFERRED EMBODIMENTS

1. Theoretical Basis of Embodiments
1.1 Definition of Waveform Parameter

Figure 4:
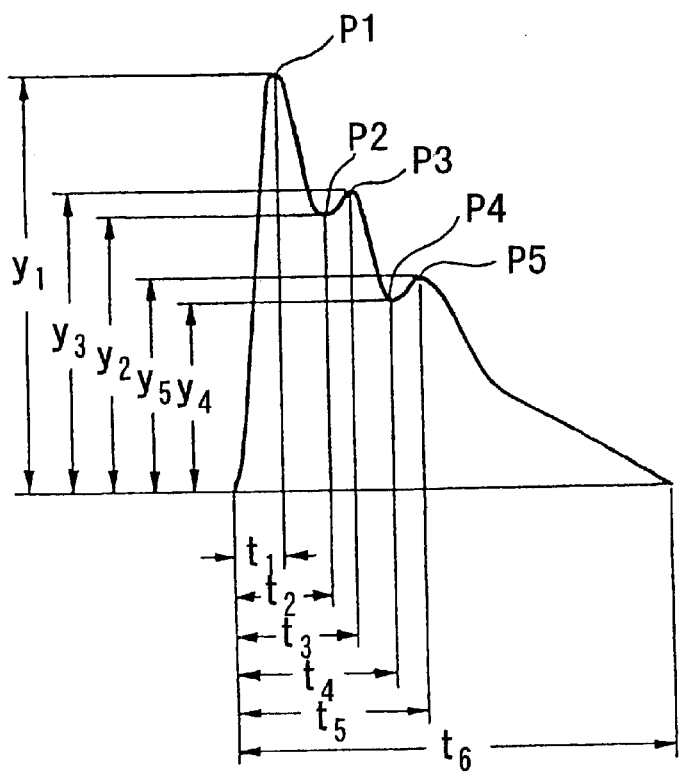
FIG. 4 shows the correspondence between waveform parameters and the waveform of a single beat in the pulse wave.

The waveform of one beat of the pulse wave has a shape as shown in FIG. 4. Blood pressure values are plotted along the vertical axis in this figure, with time noted along the horizontal axis. The following is defined as a waveform parameter for specifying the shape of this type of pulse waveform.

(1) $t_6$: time from the rise in the pulse wave corresponding to one beat (hereinafter, referred to as "pulse wave start time") until the beginning of the rise in the pulse wave corresponding to the next beat (2) $y_1 \sim y_5$: blood pressure values at maximum point P1, minimum point P2, maximum point P3, minimum point P4, and maximum point P5, which successively appear in the pulse wave (3) $t_1 \sim t_5$: elapsed time from the pulse wave start time until the appearance of points P1~P5, respectively (4) $T_{pulse}$: time (pulse wave cycle) after the appearance of point P1 until the appearance of the next point P1

1.2 Waveform Extraction Recording Member

In order to calculate the waveform parameter, information is extracted that is related to each of the aforementioned maximum and minimum points. This information is referred to as "peak information". The waveform extraction recording member described below extracts the peak information from the pulse waveforms which have been taken up. Since the details of the peak information are related to the structure and operation of the waveform extraction recording member, a more detailed description thereof will be made when the structure of the circuit is explained.

1.3 Pulse Wave Sensor (sensor unit 102)

(1) Structure and Operation

Figure 3:
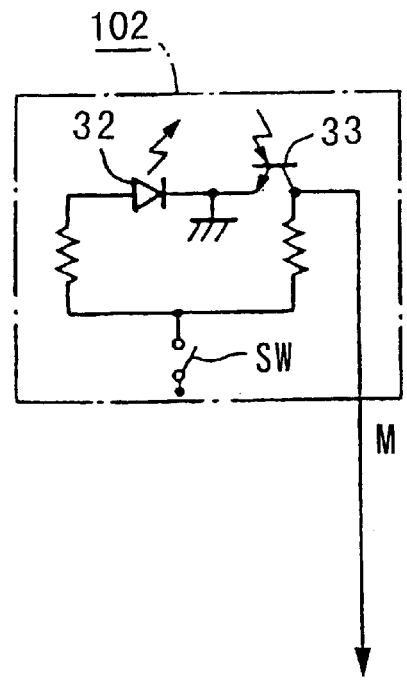
FIG. 3 is a circuit diagram of the photoelectric pulse wave sensor (sensor unit 102).

A photoelectric pulse wave sensor is available as one example of a pulse wave sensor employing light. FIG. 3 shows the structure of sensor unit 102. In this figure, 32 is a blue light emitting diode. Photo sensor 33 is formed from a phototransistor or the like.

It has typically been the practice to employ a light emitting diode that uses near infrared light, which has excellent transmission properties with respect to the human body, as a photoelectric pulse wave sensor. However, because there is also a high likelihood that light from the external environment will enter sensor unit 102 via the body, a blue light emitting diode is employed in this embodiment. Of course, the wavelength of light emitting diode 32 may be optionally selected, provided that absorption by hemoglobin is not impaired.

Light irradiated from light emitting diode 32 is absorbed by hemoglobin in the red blood cells inside the vessels directly under the surface of the skin which is in contact with sensor unit 102. The amount of light reflected back by the tissue under the skin will vary. This reflected light is received by light sensor 33, so that a pulse wave detection signal M is received as the result of photoelectric conversion.

(2) Power Conservation

When this pulse wave sensor is incorporated in a battery-operated wristwatch, for example, it is preferable to drive the battery source of sensor unit 102 only when pulse wave measurements must be made. Thus, power consumption can be reduced. For this purpose, a switch such as indicated by symbol SW in FIG. 3 is provided along the line supplying the power source to the pulse wave sensor. A switch drive circuit, not shown, switches each switch on or off, to supply an intermittent electric source to the sensors, etc.

For example, while the battery-operated wristwatch is employed as a regular wristwatch only, switch SW is in the off position, and an electric source is not supplied to sensor unit 102. On the other hand, when the pulse wave must be measured, switch SW is turned to the ON position, thereby supplying an electric source to sensor unit 102.

2. Embodiment 1

2.1 Hardware Design (1) Structure of Personal Computer

Figure 1:
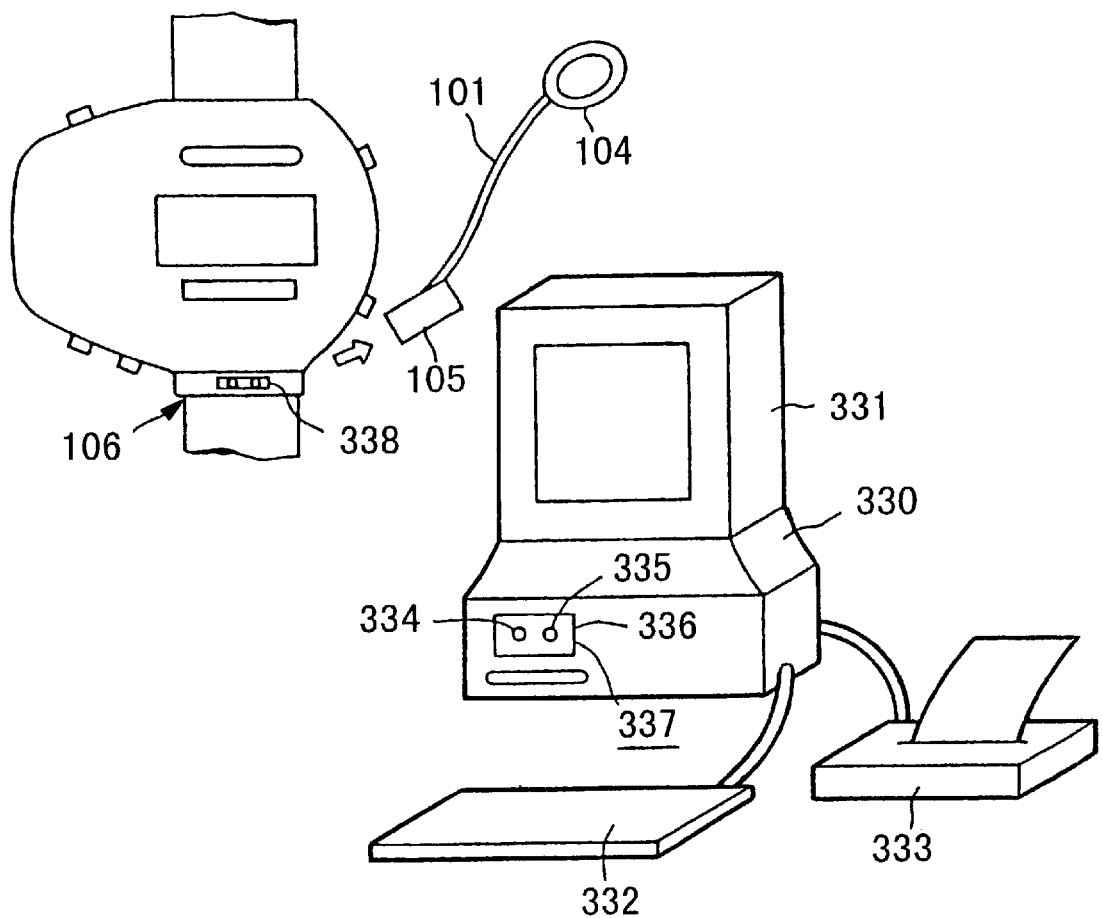
FIG. 1 shows a wristwatch incorporating the device according to the first and second embodiments of the present invention, and a personal computer which carries out optical communications with the device.

The first embodiment according to the present invention will now be explained with reference to FIG. 1. In the figure, the physiological state measuring device according to this embodiment comprises a personal computer, and a wristwatch worn by the subject. The personal computer is made up of a device main body 330, display 331, key board 332, printer 333, and the like, and, with the exception of the following points, is an ordinary personal computer. Accordingly, a detailed description of its internal structure will be omitted.

Namely, device main body 330 internally houses a transmission controller and a receiving controller, which are not shown in the figures, for sending and receiving data by means of optical signals. The transmission controller is provided with LED 334 for sending optical signals, and the receiving controller is provided with a phototransistor 335 for receiving optical signals.

LED 334 and photo transistor 335 employ near infrared (having a central wavelength of 940 nm, for example), and carry out optical communications via a visible light cutting filter 336 for blocking visible light, and through a communications window 337 used for optical communications which is provided to the front surface of device main body 330.

(2) Structural Overview of Wristwatch Main Body

The structure of the wristwatch will now be explained with reference to FIGS. 10 through 12.

Figure 10:
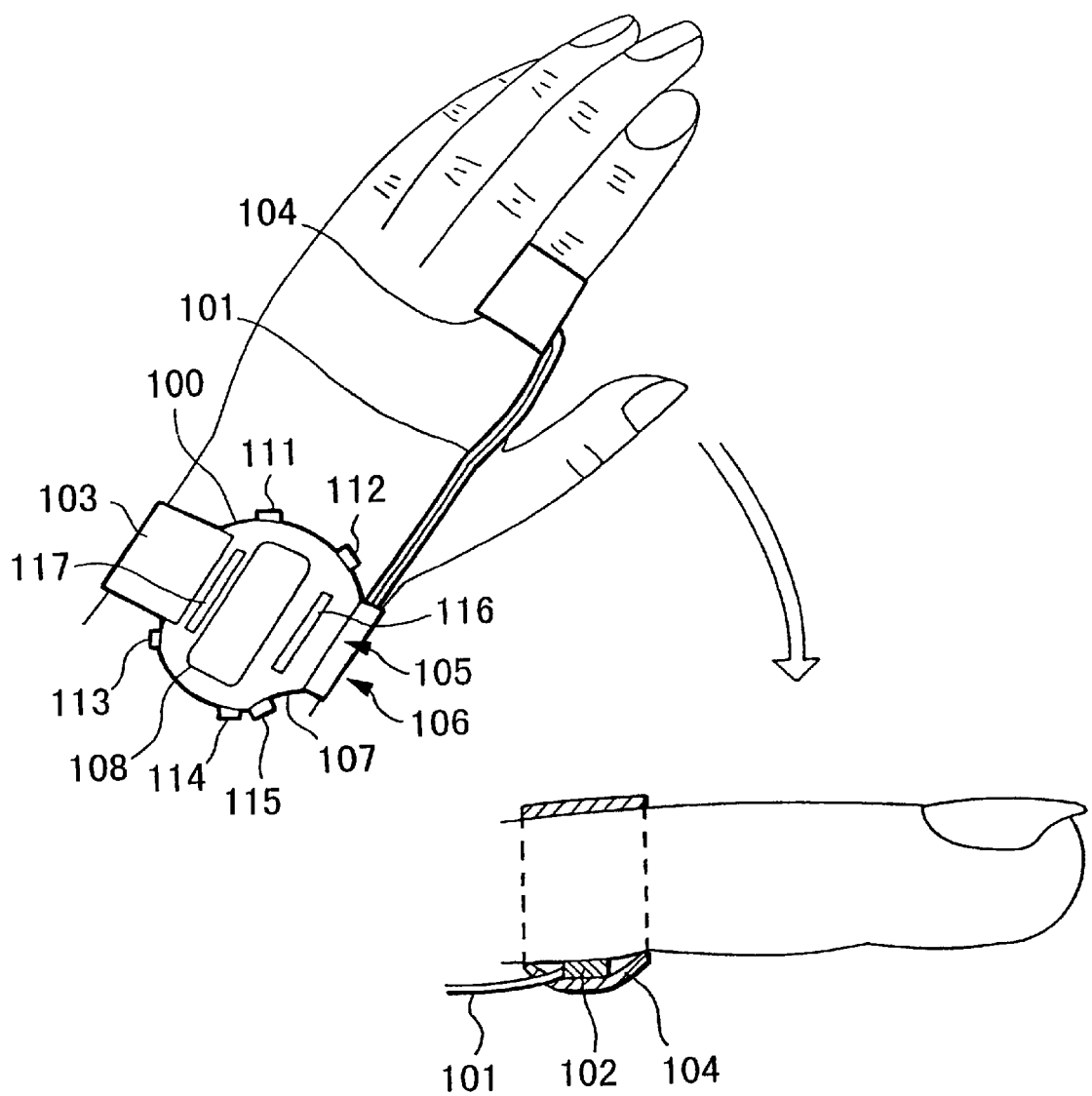
FIG. 10 shows an arrangement in which a photoelectric pulse wave sensor and a wristwatch have been combined, and the photoelectric pulse wave sensor has been attached to the base of the finger.

The wristwatch in FIG. 10 is formed of a device main body 100 which has the wristwatch structure, a cable 101 attached to device main body 100, and a sensor unit 102 provided to the end of cable 101.

A wrist band 103 is provided to device main body 100 and is wrapped around the arm from the 12 o'clock position, and fixed in place at the 6 o'clock position. This device main body 100 is designed to be freely detachable from the arm of the user by means of wrist band 103.

Light to sensor unit 102 is blocked by a band 104 for fixing the sensor in place, with sensor unit 102 attached between the base and the second joint of the index finger. When sensor unit 102 is attached to the base of the finger in this way, cable 101 can be made short, so that it does not present a hindrance to the user during exercise, for example. Additionally, it is known that when the temperature distribution from the palm to the tip of the finger is measured, the temperature at the tip of the finger drops markedly in the case where the temperature of the surrounding environment is low, whereas the temperature at the base of the finger falls comparatively little. Accordingly, if sensor unit 102 is attached to the base of the finger, accurate measurements are possible, even in the case where exercising outdoors during cold weather.

A connector 105 is provided at the 6 o'clock position on the face of the wristwatch. A connector piece 106, which is provided to the end of cable 101, is releasabley attached to connector 105. By releasing connector piece 106 from connector 105, the device may be used as an ordinary wristwatch or stopwatch. Also, in order to protect connector 105, a specific connector cover is attached when cable 101 and sensor unit 102 are released from connector 105. With the exception of an electrode component, this connector cover may be made of parts formed in the same way as connector piece 106.

As a result of a connector design described above, connector 105 is disposed toward the subject, facilitating its manipulation. In addition, since connector 105 does not extend out from device main body 100 in the 3 o'clock position, the subject can freely move his wrist during exercise. Thus, even if the subject falls during exercise, the back of the hand will not impact connector 105.

The other parts shown in FIG. 10 will now be explained in greater detail with reference given to FIG. 11. FIG. 11 shows the device main body 100 of this embodiment in detail, with cable 101 and wristband 103 detached. In this figure, parts which are equivalent to those shown in FIG. 10 have been assigned the same numeric symbol and an explanation thereof has been omitted.

Figure 11:
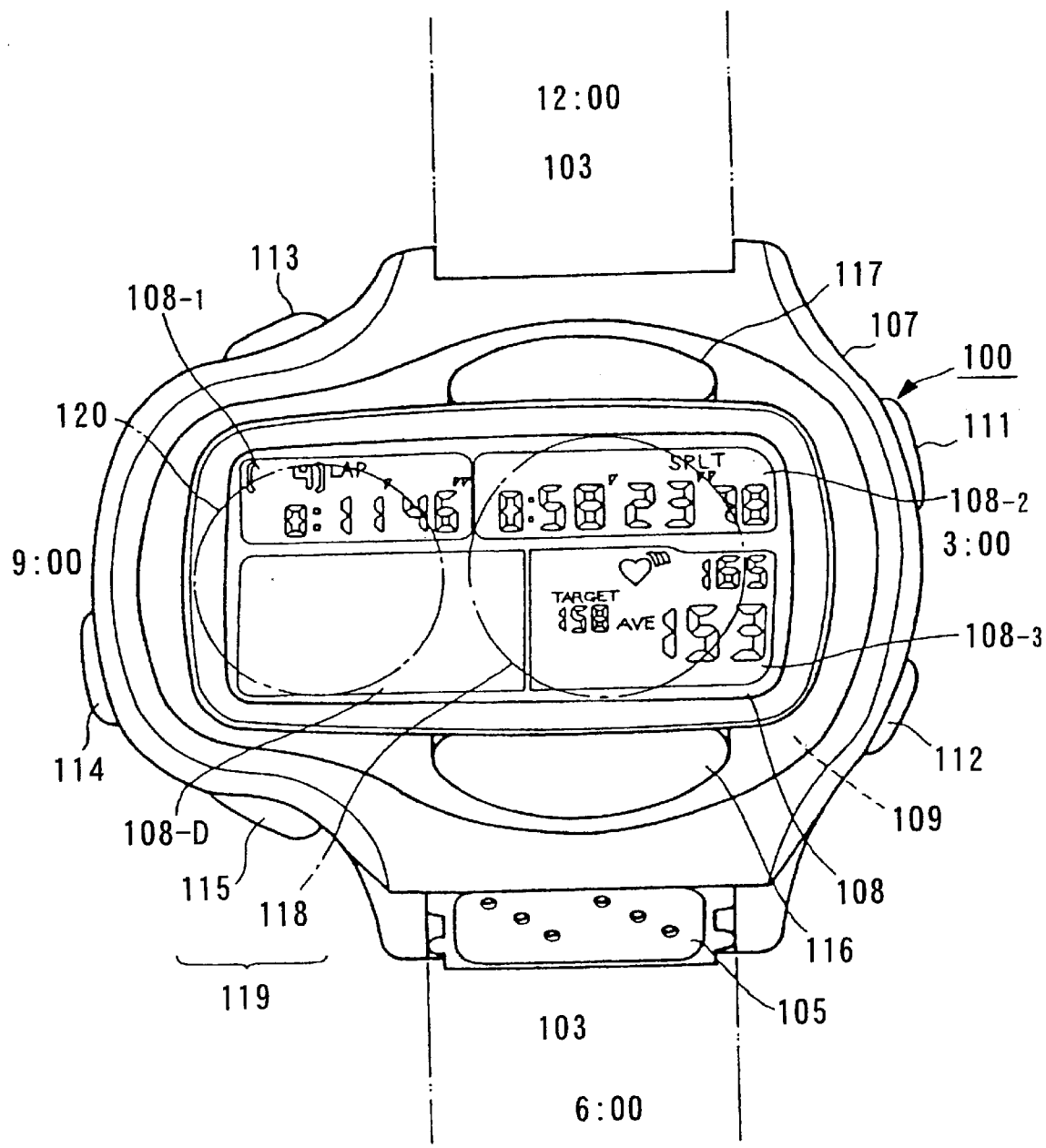
FIG. 11 is a planar view showing the structure of the wristwatch employed in the embodiment 10 in greater detail.
Figure 12:
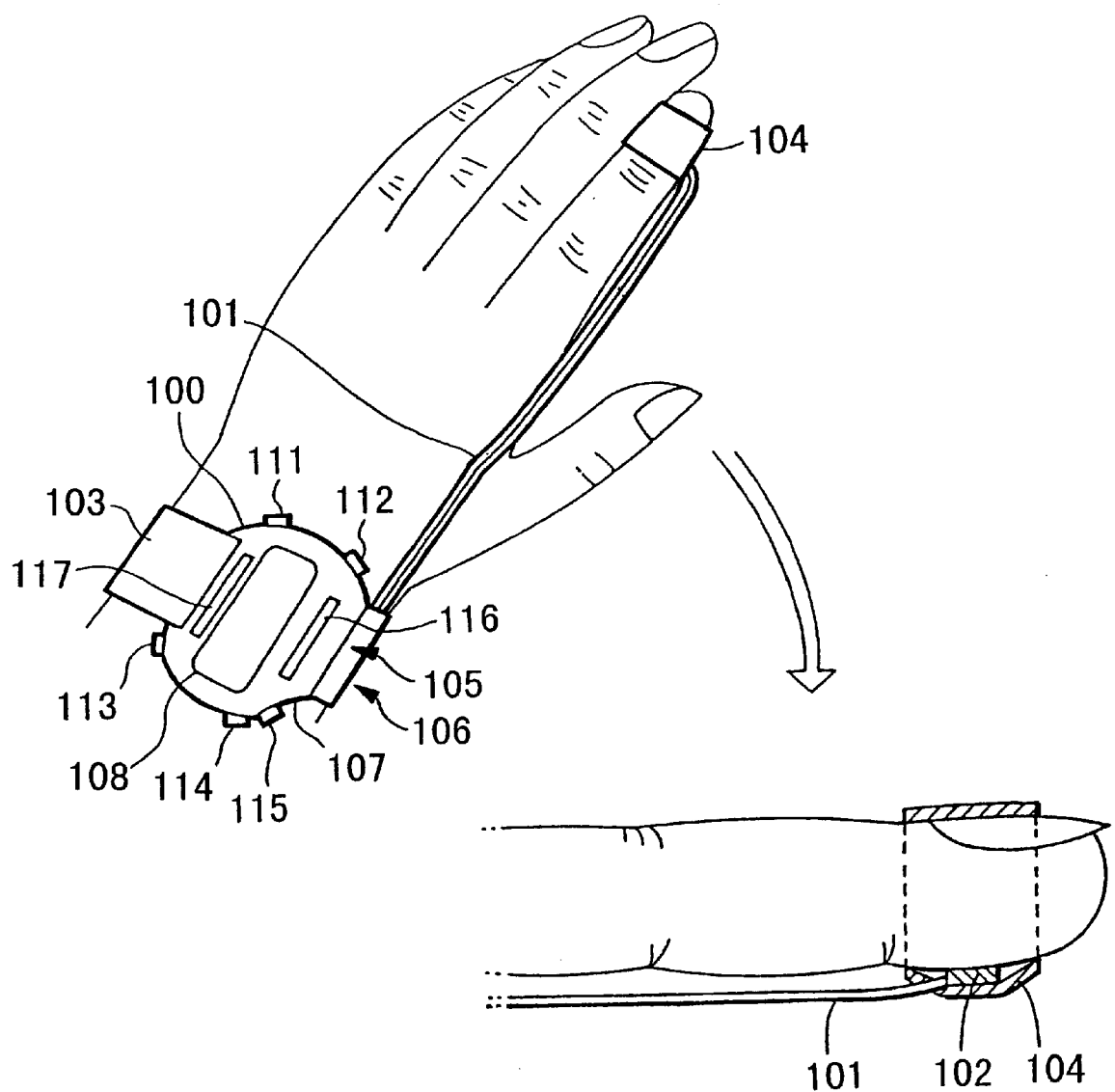
FIG. 12 shows an arrangement in which a photoelectric pulse wave sensor and a wristwatch have been combined, and the photoelectric pulse wave sensor has been attached to the fingertip.

In FIG. 11, device main body 100 is provided with a watch case 107 made of a resin. A liquid crystal display 108 is provided to the face of watch case 107 which displays in digital form the current time and date, as well as pulse wave information such as pulse and respiratory rates and the like. LCD device 108 is comprised of first, second, and third segment display regions 108-1, 108-2, and 108-3, respectively, and a dot display region 108-D. First segment display region 108-1 is positioned at the upper left area of the display panel; second segment display region 108-2 is positioned at the upper right area of the display panel; third segment display region 108-3 is positioned at the lower right area of the display panel; and dot display region 108-D is positioned at the lower left area of the display panel.

In this example, the date, day of the week and current time are displayed in first segment region 108-1, while the passage of time when carrying out various time measurements is displayed in second segment region 108-2. Various measured values obtained during measurement of the pulse wave are displayed in third segment region 108-3. Finally, various information can be graphically displayed in dot display region 108-D, in addition to a variety of other displays such as a mode display, which indicates which mode the device is in at a particular time, pulse waveform display, bar graph display, respiratory rate display, display of the change rate of the respiratory rate, or the like.

The term "mode" as used here refers to a variety of modes such as a mode for setting the time and date, a mode for using the device as a stopwatch, and a mode for operating the device as a pulse wave analysis device or a diagnostic device. These modes and the details of the display in each of the display regions described above will differ according to the application. Accordingly, explanations thereof will be made as necessary.

A controller 109 for carrying out signal processing for display on LCD device 108 is housed inside watch case 107. Controller 109 may be a one chip microcomputer or a regular microprocessor such as a CPU (central processing unit), RAM (random access memory), ROM (read-only memory) or the like. Controller 109 includes a watch circuit for carrying out watch functions. Further, an ordinary clock time display may be used for LCD device 108, however, live time or split time displays for use when the device is operated as a stop watch are also possible.

Button switches 111~117 are provided to the outer periphery and surface of watch case 107. An example of the functions of these button switches follows, however, these functions will differ depending on the device which is incorporated with the wristwatch.

When button switch 111, which is at the 2 o'clock position on the wristwatch, is pressed, an alarm is set to sound one hour thereafter.

Button switch 112, which is at the 4 o'clock position on the wristwatch, is provided for directing switching between the device's various modes.

When button switch 113, which is at the 11 o'clock position on the wristwatch, is pressed, an electroluminescence (EL) back light on liquid crystal display device 108 is turned on for 3 sec, for example, after which it automatically turns off.

Button switch 114, which is at the 8 o'clock position on the wristwatch, switches between the various graphic displays which are to be displayed on dot display region 108-D.

By pressing button switch 115, which is at the 7 o'clock position on the wristwatch, the form of time and date display (i.e., time displayed in seconds/minutes/hours, 12 or 24 hour display, year/month, date, etc.) can be switched in the day and date correction mode.

Button switch 116, which is positioned below LCD display 108, can be used when correcting time or date, by decreasing the setting by one. Additionally, when timing a lap, button switch 116 can be used as a switch for informing controller 109 of the completion each lap.

Button switch 117, which is positioned above LCD 108, is employed for indicating the initiation or termination of operation of the pulse wave analysis or diagnostic device. In addition to being used to increase the time and date settings by one, button switch 117 can also be used to indicate the initiation or termination of a variety of time elapse measurements.

A button-shaped battery 118 is housed in watch case 107 and serves as a power source for the device. Cable 101 shown in FIG. 10 supplies electric power from battery 118 to sensor unit 102, and sends the detection results from sensor unit 102 to controller 109.

It becomes necessary to enlarge device main body 100 as the functions of the watch itself are increased. Device main body 100 cannot be enlarged in the 6 or 12 o'clock directions, however, since a limitation on size is imposed because the watch must be worn on the arm. Therefore, in this embodiment, a horizontally long watch case 107 is employed which is longer in the horizontal, (i.e., 3 o'clock to 9 o'clock) direction, than in the vertical (i.e., 6 o'clock to 12 o'clock) direction.

In this embodiment, wrist band 103 is connected to a watch case 107 at a position shifted toward the 3 o'clock side of the watch. As seen from wrist band 103, a large overhang 119 is present on the 9 o'clock side the wristwatch, but is absent from the 3 o'clock side of the watch. Accordingly, the subject can bend his wrist when using or carrying the horizontally long watch case 107. Further, even if the subject falls, he will not hit the watch case with the back of his hand.

A flat piezo element 120 used as a buzzer is disposed inside the watch case 107, at the 9 o'clock position with respect to the battery 118. Battery 118 is heavier than piezo element 120, such that the position of the weight center of device main body 100 shifts toward the 3 o'clock side. Moreover, wrist band 103 is connected to the side of the main body 100 toward which the weight center has shifted. As a result, device main body 100 can be attached to the arm in a stable manner.

Further, since battery 118 and piezo element 120 are disposed in the planar direction, device main body 100 may be made thinner. By providing a battery cover to the rear surface of the wristwatch, the subject can easily change the battery.

An acceleration sensor, not shown in the figures, is provided inside the wristwatch. Accordingly, when the subject moves his arms, the acceleration of the wristwatch is detected by the acceleration sensor.

Connector 105 is designed to be freely releasable from device main body 100 of the wristwatch. Thus, in place of the connector cover, a communications connector 338 such as shown in FIG. 1 may be attached to the connector portion when connector 105 is removed in order to enable communications between the wristwatch and the personal computer.

As in the case of the personal computer, an LED, photo transistor, and interface for optical communications are incorporated in communications cover 338. An optical interface (not shown) is provided inside device main body 100 of the wristwatch, in order to carry out optical communications.

(3) Waveform Extraction Recording Member 180 Housed Inside Wristwatch (3-1) Circuit Structure Waveform extraction memory 180 (see FIG. 5) is attached inside the wristwatch, and carries out pulse wave analysis. A detailed explanation of its structure will now be made with reference to FIG. 5.

Figure 5:
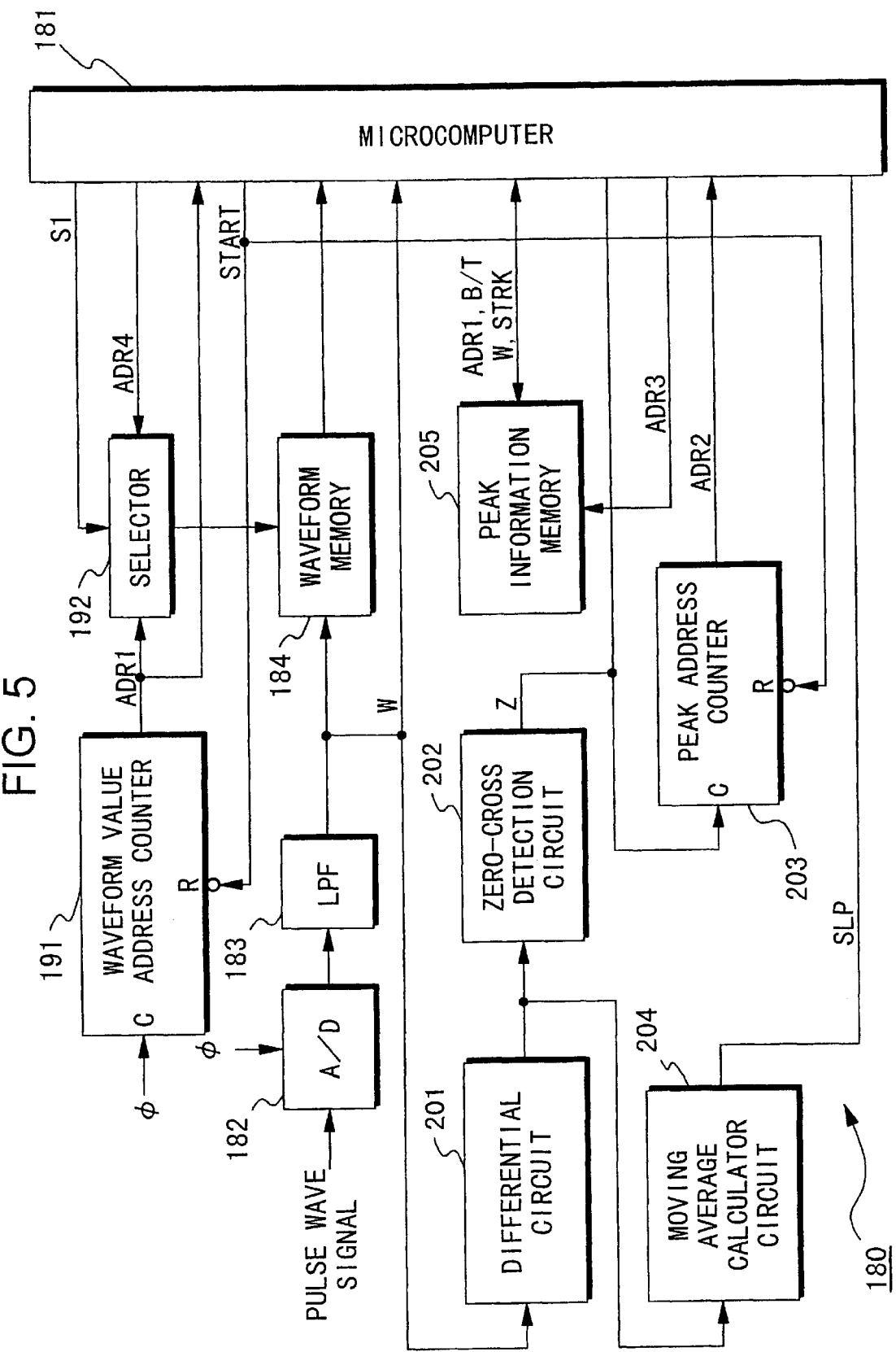
FIG. 5 is a block diagram showing the structure of parameter extracting member 180.

In FIG. 5, 181 is a microcomputer which controls the overall operation of the wristwatch. 182 is an A/D converter which converts the pulse wave signal input from the wristwatch via the receiving controller described above to a digital signal in accordance with a fixed cycle sampling clock $\phi$.

The numeric symbol 183 indicates a low pass filter which removes from the digital signals sequentially output from A/D converter 182 those components which exceed a specified cut-off frequency, and sequentially outputs this result as waveform value W.

The numeric symbol 184 indicates a waveform memory formed of RAM which sequentially stores the waveform values W supplied via a low pass filter 183.

The numeric symbol 191 is a waveform value address counter which starts counting the sampling clock φ during the time period in which microcomputer 181 outputs a START directive to begin collecting the pulse waves. Waveform value address counter 191 outputs the counter result as the waveform value address ADR1 where waveform value W is to be written. This waveform value address ADR1 is monitored by microcomputer 181.

The numeric symbol 192 indicates a selector. When microcomputer 181 is not outputting a select signal S1, selector 192 selects the waveform value address ADR1 output by waveform value address counter 191, and supplies the selected waveform value address ADR1 to the address input terminal of waveform memory 184. In contrast, when a select signal S1 is being output by microcomputer 181, selector 192 selects the readout address ADR4 which is output by microcomputer 181, and supplies the selected readout address ADR4 to the address input terminal of waveform memory 184.

The numeral 201 in the figure indicates a differential circuit which calculates the time derivative of the waveform values W which are sequentially output from low pass filter 183.

202 is a zero cross detection circuit which outputs zero cross detection pulse Z when the time derivative of waveform value W is 0 due to the presence of a maximum or minimum waveform value W. More precisely, zero cross detection circuit 202 is provided to detect peaks P1, P2, . . . in the waveform of the pulse wave disclosed in FIG. 6. Zero cross detection pulse Z is output when waveform values W corresponding to these peaks are input.

203 is a peak address counter. Peak address counter 203 counts zero cross detection pulse Z while microcomputer 181 is outputting a START directive to begin collecting the pulse waves. Peak address counter 203 then outputs the counted result as peak address ADR2.

204 is a moving average calculator circuit which calculates the average value of the time derivative of a fixed number of past waveform values W output from differential circuit 201 through the present point in time. The calculated result is output as slope information SLP indicating the slope of the pulse wave up through the current point in time.

Figures 6, 7:
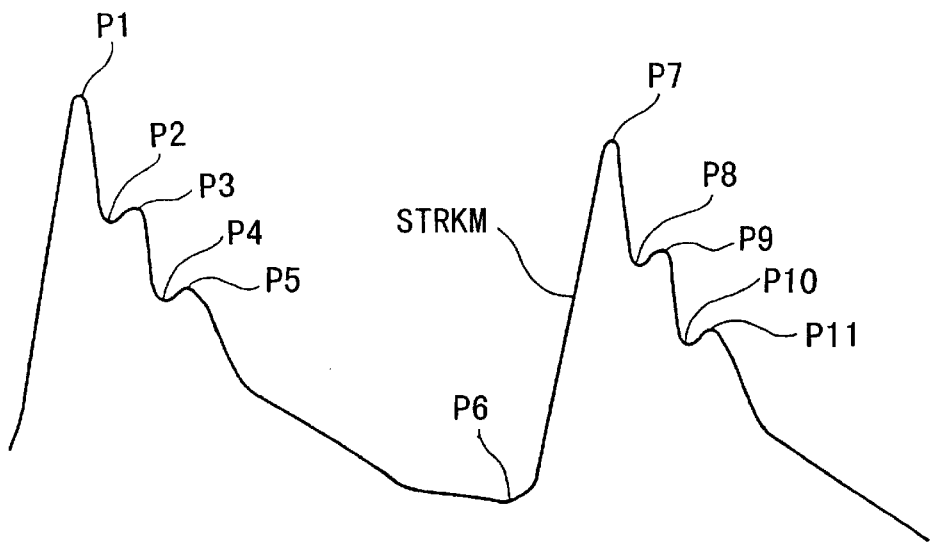
FIG. 6 shows an example of the radius artery waveform stored in waveform memory 184.
FIG. 7 shows the memory contents of peak information memory 205.

205 indicates peak information memory provided to store the peak information explained below. Peak information will be explained in greater detail below. Namely, the details regarding peak information shown in FIG. 7 are listed as follows.

1. Waveform Value Address ADR1

The waveform value address ADR1 is the write address output from waveform value address counter 191 when the waveform value W output from low pass filter 183 is a maximum or minimum value. In other words, this is the write address in waveform memory 184 for waveform value W corresponding to a maximum or minimum value.

2. Peak Type B/T

The peak type is information indicating whether waveform value W which is written in waveform value address ADR1 is a maximum value T (Top) or a minimum value B (Bottom).

3. Waveform Value W

This is the waveform value corresponding to the maximum or minimum values.

4. Stroke Information STRK

The stroke information STRK is the amount of change in the waveform value from the immediately preceding peak value to the relevant peak value.

5. Slope Information SLP

This is the average value of the time derivative of a fixed number of past waveform values up through the relevant peak value.

(3-2) Operation of Circuit

The operations of waveform extraction memory 180 under the control of microcomputer 181 will now be explained.

(a) Collection of Waveform and Peak Information

When microcomputer 181 outputs a START directive to begin collecting waveforms, waveform value address counter 191 and peak address counter 203 cease to be reset.

As a result, the sampling clock φ counter is started by waveform value address counter 191. The counter value is supplied to waveform memory 184 via selector 192 as waveform value address ADR1. The pulse wave signals supplied from the wristwatch are input to A/D converter 182, and sequentially converted to digital signals in accordance with the sampling clock φ. These converted digital signals are then sequentially output via low pass filter 183 as waveform values W.

The waveform values W output in this way are sequentially supplied to waveform memory 184, and written in the memory area specified by waveform value address ADR1 at that point in time. As a result of the preceding operations, a continuous waveform value W corresponding to the waveform of the radius artery is stored in waveform memory 184. This continuous waveform value W is shown in FIG. 6.

In parallel with the preceding operation, detection of peak information and writing to peak information memory 205 are carried out as explained below.

First, the time derivative of the waveform values W output from low pass filter 183 is calculated by differential circuit 201, and then input to zero cross detection circuit 202 and moving average calculator circuit 204. Moving average calculator circuit 204 calculates the average value (i.e., moving average value) of a specified past number of time derivatives each time the time derivative of a waveform value W is supplied, and outputs the calculated result as slope information SLP.

A positive value will be output for slope information SLP when waveform value W has finished rising and reached a maximum value. Conversely, a negative value will be output for slope information SLP when waveform value W is falling or has fallen to a minimum value.

When waveform value W corresponding to maximum point P1 shown in FIG. 6, for example, is output from low pass filter 183, 0 is output from differential circuit 201 as the time derivative, and zero cross detection pulse Z is output from zero cross detection circuit 202.

As a result, microcomputer 181 uptakes at that point in time waveform address ADR1, which is the counter value of waveform value address counter 191; waveform value W; peak address ADR2, which is the counter value of the peak address counter (here, ADR2=0); and slope information SLP. Further, when zero cross detection pulse Z is output, the counter value ADR2 of peak address counter 203 becomes 1.

Microcomputer 181 creates peak type B/T based on the sign of the uptaken slope information SLP. In this case, when the waveform value W of maximum value P1 is output, then positive slope information is output at that point in time. As a result, microcomputer 181 sets the value of peak information B/T to one corresponding to a maximum value.

Microcomputer 181 indicates peak address ADR2 taken up from peak address counter 203 (here ADR2=0) as write address ADR3 without any modification, and writes waveform value W, its waveform address ADR1, peak type B/T, and slope information SLP as first time peak information in peak information memory 205. When writing first time peak information, stroke information STRK is not created or written since there is no immediately preceding peak information.

When waveform value W corresponding to minimum point P2 shown in FIG. 6 is subsequently output from low pass filter 183, for example, zero cross detection pulse Z is output in the same way as above, and write address ADR1, waveform value W, peak address ADR2 (=1), and slope information SLP (<0) are taken up by microcomputer 181.

Next, in the same manner as above, microcomputer 181 determines the peak type B/T (B, in this case) based on slope information SLP. Next, the address which is 1 less than peak address ADR2 is read out by microcomputer 181, and supplied to peak information memory 205 as address ADR3. The waveform value W which was written first is then read out. Next, microcomputer 181 calculates the difference between the current waveform value W taken up from low pass filter 183 and the waveform value W read out from peak information memory 205 which was taken up first. As a result, stroke information STRK is obtained.

The thus obtained peak type B/T and stroke information STRK are written in the recording area corresponding to peak address ADR3=1 in peak information memory 205 as the second peak information, along with other information such as waveform value address ADR1, waveform value W and slope information SLP. Thereafter, the same operation is carried out when peaks P3, P4, . . . , are detected.

Once a specific period of time has elapsed, microcomputer 181 stops outputting the waveform collection directive START, and the collection of waveform value W and peak information terminates.

(b) Pulse Waveform Partitioning Processing

From among the various information stored in peak information memory 205, microcomputer 181 carries out processing to specify the information corresponding to the waveform of a single beat at which waveform parameter collection is performed.

First, slope information SLP and stroke information STRK corresponding to each of the peaks P1, P2, . . . are sequentially read out from peak information memory 205. Next, stroke information corresponding to positive slopes is selected from each stroke information STRK (i.e., the corresponding slope information SLP which is positive). A specified number of the largest values are then selected from among this stroke information.

Next, stroke information corresponding to middle values is selected from among the selected stroke information STRK, and the stroke information for the rising portion (for example, the rising portion indicated by the letters STRKM in FIG. 6) of the pulse wave of one beat at which waveform parameter extraction is to be carried out is obtained. Next, the peak address preceding the peak address of this slope information (i.e., the peak address at point P6, the initiation of the pulse wave of one beat at which waveform parameter extraction is to be performed) is obtained.

(c) Extraction of Waveform Parameters

Microcomputer 181 calculates each waveform parameter by referencing each peak information corresponding to the pulse wave of one beat recorded in peak information memory 205. This processing may be obtained as follows.

1. blood pressure values $y_1 \sim y_5$

The waveform values corresponding to peaks P7~P11 are defined as $y_1 \sim y_5$ respectively 2. time $t_1$ The waveform address corresponding to peak P6 is subtracted from the waveform address corresponding to peak P7. $t_1$ is calculated by multiplying the cycle of the sampling clock $\phi$ with this result.

3. time $t_2 \sim t_6$ and pulse wave cycle $T_{pulse}$

As in the case of $t_1$ above, $t_2 \sim t_6$ are calculated based on the difference in the waveform addresses between each of the corresponding peaks.

Further, each of the waveform parameters obtained in this way are stored in the buffer memory inside microcomputer 181.

(d) Spectrum Analysis of the Fluctuation

Microcomputer 181 stores blood pressure values $y_1$ over a specific time interval (for example, 30 seconds to 1 minute). Namely, microcomputer 181 stores blood pressure values in the interval between the two broken lines in FIG. 8. However, because the obtained blood pressure value $y_1$ is discrete along the time axis, a suitable interpolation method is employed to interpolate between adjacent blood pressure values $y_1$, to obtain a curved line such as shown in FIG. 9(a). This curved line is referred to a the "fingertip plethysmogram envelope". When FFT is carried out on the fingertip plethysmogram envelope, a spectrum such as shown in FIG. 9(b) is obtained.

In this figure, the frequency spectrum of the fingertip plethysmogram envelope includes the following components.

1. HF (high frequency) component which is the fluctuation coinciding with respiration
2. LF (low frequency) component which fluctuates on a cycle of around 10 seconds
3. Trend which fluctuates at a very low frequency The conventional device obtained the subject's respiratory rate by detecting the HF component from among the peak values in the frequency spectrum. However, since the frequency spectrum shown in FIG. 9(b) is for a subject at rest, a body motion component (hereinafter, referred to as "body motion spectrum") will be superimposed on the fingertip plethysmogram envelope if the subject is exercising. Since the level of this component is higher than the component corresponding to the respiratory rate, it is difficult to accurately detect the HF component.

(e) Removal of Body Motion Spectrum

An acceleration sensor is provided to a wristwatch in this embodiment. Namely, when an output signal from the acceleration sensor is supplied to microcomputer 181, microcomputer 181 removes the acceleration frequency and the harmonic component thereof from the entire frequency spectrum. As a result, the portion corresponding to the body motion spectrum is removed.

(f) Filtering

In some cases it may not be possible to completely remove the body motion spectrum from the frequency of the signal output from the acceleration sensor, and its harmonic component. Therefore, in this embodiment, a "window function" which shifts according to the pulse rate $N_{pulse}$, is employed for the frequency spectrum (i.e., band pass filtering is performed). As a result, the range in which the HF component is believed to be present is extracted, and the effect of components outside this area is removed.

This window function (transmission region) is set according to the range $[(1-\delta_1)\alpha_0 N_{pulse} \sim (1+\delta_2)\alpha_0 N_{pulse}] \cdot \alpha_0$ here is the ratio of the pulse rate $N_{pulse}$ to the subject's typical respiratory rate (i.e., pulse to respiratory rate ratio). A value in the range of [4+−0.5] may be employed depending on the subject. $\delta_1$ and $\delta_2$ are constants indicating the extent of dispersion in the actual values with respect to the typical pulse to respiratory rate ratio $\alpha_0$. A setting of around [0.5] is suitable. A conventional digital filtering technique may be employed for the filtering recited here.

When a frequency spectrum is obtained which has been filtered and which has had the body motion spectrum arising from exercise or daily activity removed, the peak values (maximum level frequency components) of that frequency spectrum are detected. The detected components are the components corresponding to the respiratory rate. The detected respiratory rate is stored in microcomputer 181, and sent to device main body 330 of the personal computer via a transmitter.

(g) Rate of Change Calculation

Next, microcomputer 181 calculates the rate of change in the detected respiratory rate, and compares this value to predetermined threshold values. The rate of change in this respiratory rate may be employed as an indicator showing the degree of mental relaxation, so that the degree of relaxation may be determined based on the results of this comparison.

(h) Communication of Physiological State

In order to send various information stored in the hard disk or RAM of the personal computer to the wristwatch, a transmit command is input from keyboard 332, for example. As a result, the information in the personal computer is output as near infrared light via LED 334 and communications window 337. This near infrared light is sent to the optical interface of the wristwatch via communications connector 338.

When sending various information such as the measured values of physiological state to the personal computer from the wristwatch, the direction of communication is the opposite of that described above. Namely, the user of the portable device operates a button switch provided to the wristwatch, to set the portable device in the data transmission mode.

As a result, the processor stored in the device reads out the information to be sent from the RAM or the like, and relays this to the optical interface. As a result, the measured value is converted to an optical signal and sent from communications connector 338 to the personal computer via communications window 337 and photo transistor 335.

A mode for sending one-time only data (singleness transmission mode) and a mode for automatically sending data at specific time intervals, every few seconds or every 20 or 30 seconds, for example, (interval transmission mode), are provided as the data transmission modes for the personal computer and the wristwatch. When diagnosis is carried out by the personal computer using the respiratory rate and the pulse waveform, this data must be intermittently sent to the personal computer. Therefore, the intermittent transmission mode is employed. When sending this data, data compression is performed.

However, when a plurality of personal computers or wristwatches are carrying out the above-described optical communications, then it becomes impossible to identify which device generated which information. Accordingly, in conventional devices, information intended for one device was sometimes mistakenly received by another device. Therefore, when sending or receiving information, recognition information indicating which device generated the information is employed in the I/O interface means of the present invention.

Figure 2:
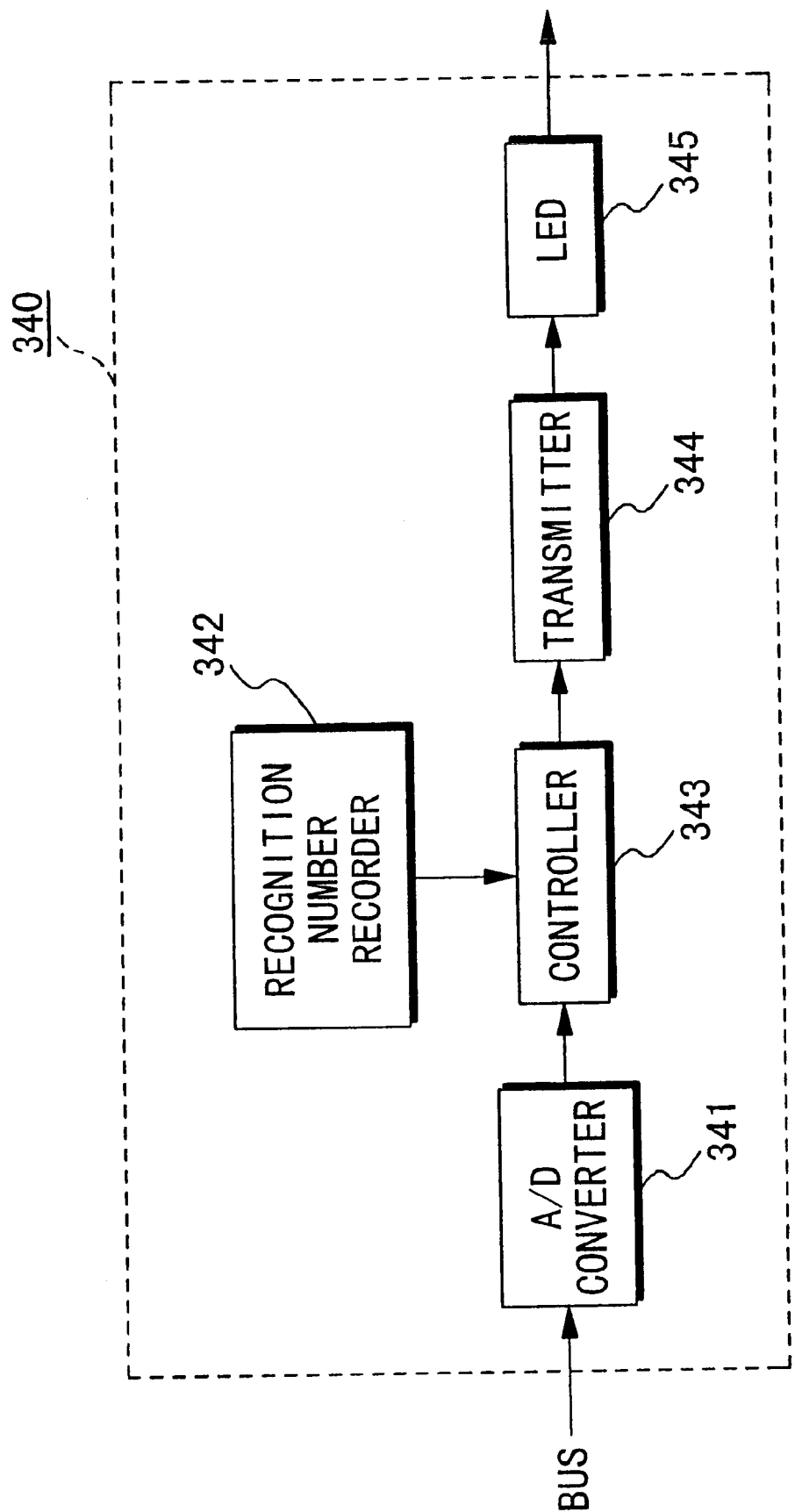
FIG. 2 is a detailed block diagram showing the transmission device provided inside the input/output interface incorporated in the device according to the first and second embodiments of the present invention.

The design employed to prevent competition when a plurality of devices are sending optical signals will now be explained with reference to FIG. 2. Transmitter 340 shown in this figure is stored in the I/O interface means. Information from the processor in the personal computer or the portable device is stored in a bus.

A/D converter 341 samples and converts the information signals sent from the bus into digital signals at fixed time intervals.

Recognition number recorder 342 records the recognition number for recognizing which device sent the optical signal. When the information is sent outside transmission device 340, this recognition number is included in the optical signal together with the aforementioned information. Since the recognition numbers recorded in the recognition number recorders 342 of each transmission device 340 differ depending on the settings at the time of shipment of the devices, a unique number is assigned to all of the devices, including the portable device, the personal computer and the like.

Controller 343 is a circuit for controlling all parts inside transmitter 340. Transmitter 344 houses a drive circuit for driving LED 345 which relays the optical signal. By driving LED 345, transmission data formed by controller 343 is sent to the outside after conversion to an optical signal.

By enabling communication between the portable device and the external device in this way, it is possible to send information from the portable device to the external device, as well as to carry out a variety of settings or displays from the external device to the portable device.

Lastly, transmission of information between the portable device and the external device will now be explained using a specific example. A pulse waveform measured by the portable device is displayed on display 331 provided to the external device (see FIG. 1). Normal, smooth or violent waves are the types of waveforms which may be displayed on display 331. The type of measured pulse waveform is sent from the portable device to the external device, after being compressed at the portable device end.

In order to realize the above, the pulse waveform measured in the body is analyzed at the portable device and determined to be a normal, smooth or violent wave. This determination may be made, for example, by investigating the correlation between pulse wave distortion (or circulatory state parameters) and the normal, smooth and violent waves, calculating the pulse wave distortion (or the circulatory state parameter) from the measured pulse wave, and determining the type of pulse wave. The respiratory rate is calculated at the portable device.

Next, this information is then encoded to a character code, for example, in response to the type of pulse wave. The encoded information is then sent to the external device as optical communications via respective I/O interfaces provided to the portable and external devices. The external device recognizes whether the wave is a normal, smooth or violent wave based on the encoded information relayed to it. The pulse waveform corresponding to the waveform type recognized is read out from a ROM or the like stored in the external device, and displayed on display device 331.

In addition to displaying the pulse waveform in this way, display device 331 may also be used to display the respiratory rate, or the name corresponding to the classified waveform, i.e., normal, smooth, or violent, in letters. Alternatively, this information may be displayed using symbols or icons.

Further, if a design is provided for realizing communication using compressed information between the portable device and the external device, then the amount of information to be relayed can be decreased. Please note that communication involving compressed information is equivalent to the case where information is relayed from the external device to the portable device.

2.2 Functional Structure

The functional structure of the first embodiment will now be explained. FIG. 21 is a block diagram showing the functional structure of the first embodiment. In this figure, 11 is an acceleration sensor which detects a body motion waveform TH expressing the subject's body motion. The above-described sensor unit 102 is formed of an optical pulse wave sensor and detects the subjects pulse waveform. The numerals 10 and 12 indicate first and second FFT processors, respectively, which are formed of a microcomputer 181 such as described above. First FFT processor 10 carries out FFT processing on pulse waveform MH, to generate pulse wave analysis data MFD. Second FFT processor 31 carries out FFT processing on body motion waveform TH to generate body motion analysis data TFD.

Next, body motion removing member 13 removes the spectrum frequency component corresponding to each of the spectrum frequencies in the body motion analysis data TFD from among each of the spectrum frequency components of the pulse wave analysis data MFD, to generate pulse wave analysis data MKD from which body motion has been removed. The maximum peak frequency in the low frequency region of pulse wave analysis data MKD from which body motion has been removed is the fundamental frequency Fv1 of the respiratory component. The maximum peak frequency in the high frequency region of the pulse wave analysis data MKD from which body motion has been removed is the fundamental frequency Fm1 of the pulse wave.

Figure 22A:
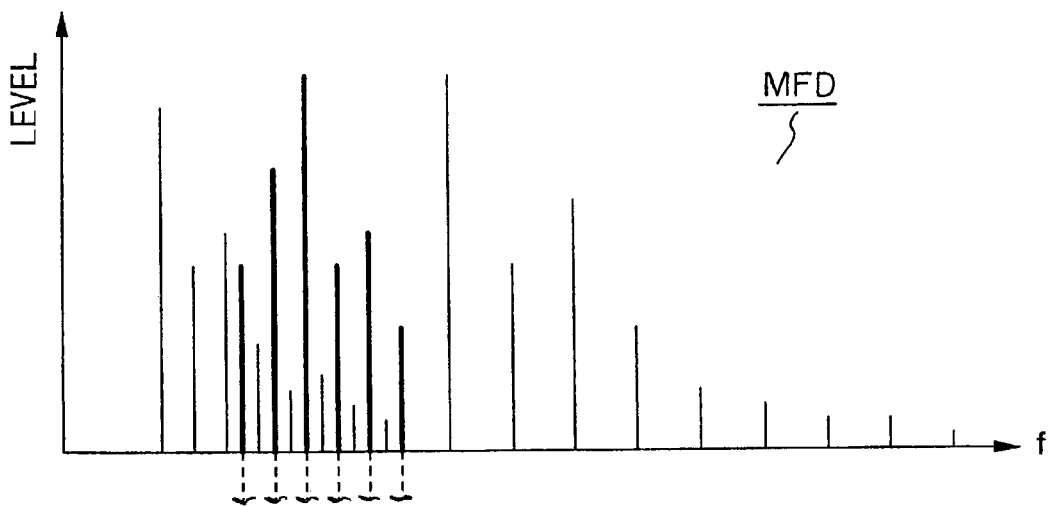
FIGS. 22A, 22B and 22C show an example of the relationship between pulse wave analysis date MFD, body motion analysis date TFD and pulse wave analysis data MKD from which body motion has been removed, according to the same embodiment.
Figure 22B:
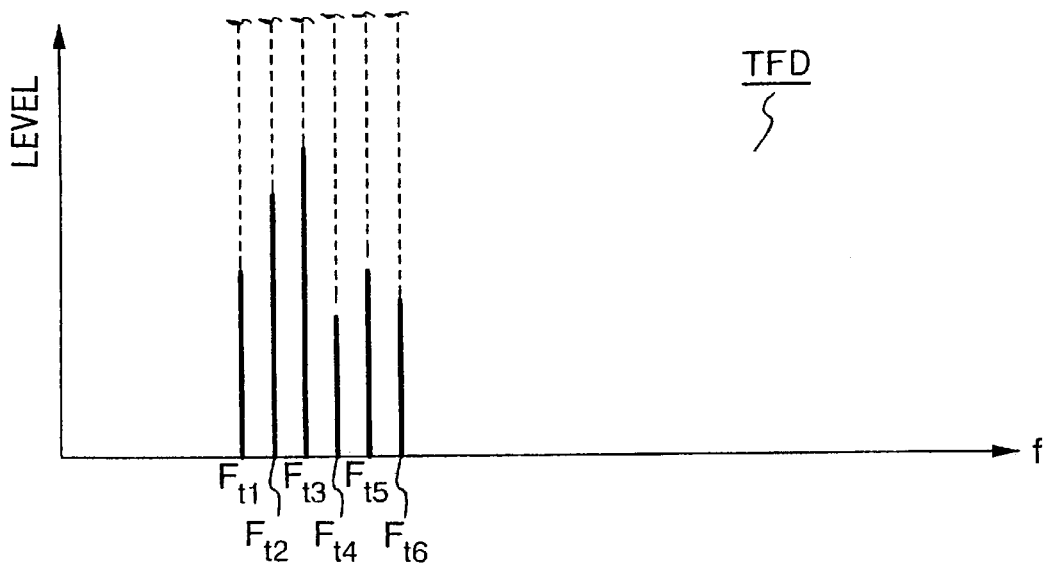
Figure 22C:
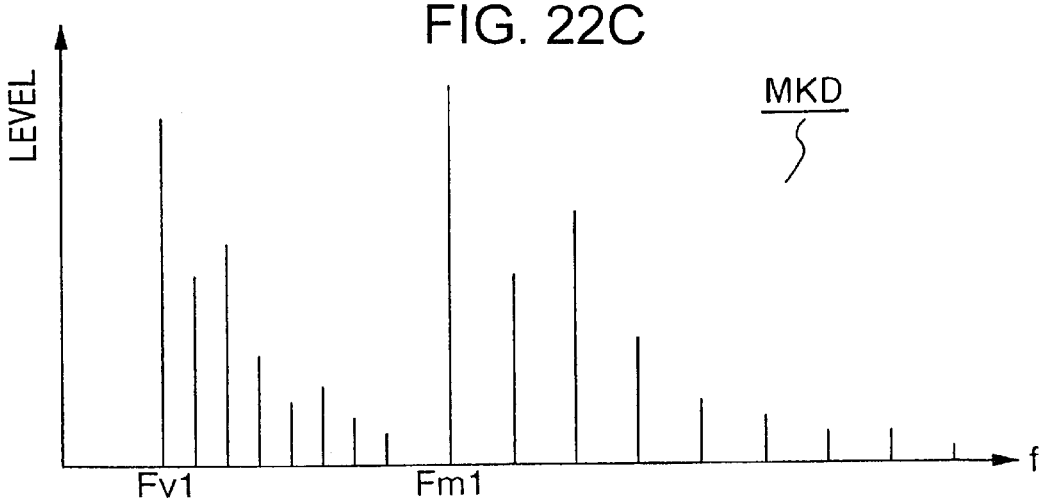

FIGS. 22A, 22B and 22C show an example of the relationship between pulse wave analysis data MFD, body motion analysis data TFD and pulse wave analysis data MKD from which body motion has been removed. The operation to remove body motion will be explained using this figure. FIG. 22($a$) shows the details of pulse wave analysis data MFD, and FIG. 22($b$) shows the details of the body motion analysis data TFD. Body motion removing member 13 specifies each of the spectrum frequencies Ft1~Ft6 shown in FIG. 22($b$) based on the body motion analysis data TFD. Body motion removing member 13 removes the spectrum frequency components corresponding to the spectrum frequencies Ft1~Ft6 from among the spectrum frequency components of the pulse wave analysis data MFD, and generates pulse wave analysis data MKD from which body motion has been removed shown in FIG. 22($c$).

Body motion waveform TH is detected as the acceleration in arm movement, for example. Because blood flow is effected by the vessels and tissues, however, the body motion component of pulse wave analysis data MFD and the body motion analysis data TFD are not equivalent. Specifically, as shown in FIGS. 22($b$) and 22($a$), each of the spectrum frequency components corresponding to spectrum frequencies Ft1~Ft6 differ with respect to pulse wave analysis data MFD and body motion analysis data TFD. For this reason, in this example, body motion analysis data TFD is not subtracted from pulse wave analysis data MFD, but rather the spectrum frequency components corresponding to spectrum frequencies Ft1~Ft6 are removed. In addition, by also carrying out filtering at body motion removing member 13, it is possible to even more accurately remove the body motion component.

Next, pulse and respiratory rate extracting member 14 specifies the maximum peak frequency from among each of the spectrum frequency components based on pulse wave analysis data MKD from which the body motion component has been removed. The energy of the pulse wave component is greater than the energy of the respiratory component. Therefore, the maximum peak frequency specified here corresponds to fundamental frequency Fm1 shown in FIG. 22($c$). Pulse and respiratory rate extracting member 14 generates pulse rate information MJ by calculating 60/Fm1.

Pulse and respiratory rate extracting member 14 extracts the fundamental frequency Fv1 of the respiratory component by specifying the maximum peak frequency which is less than Fm1, and then calculates 60/Fv1 in order to generate respiratory rate information KJ. Pulse rate information MJ and respiratory rate information KJ are relayed to the personal computer and supplied to display 17.

Next, a given sampling time is defined as Tn and the sampling time immediately preceding it is defined as Tn−1. Then, rate-of-change-in-respiratory-rate calculating member 15 calculates the rate-of-change-in-respiratory-rate information KJ' using the following formula, sends this information to the personal computer, and supplies it to display 17.

$$KJ'(Tn)=\{KJ(Tn)-KJ(Tn-1)\}/KJ(Tn)$$

The above equation is one example for calculating rate-of-change-in-respiratory-rate information KJ'. Other examples include measuring the respiratory rate over a specific time interval (one minute, for example), and calculating the rate-of-change-in-respiratory-rate information KJ' based on the measured result and the respiratory rate measured during the immediately preceding detection.

Next, comparing member 16 compares rate-of-change-in-respiratory-rate information KJ' with predetermined threshold values R1 and R2, and generates message information. Threshold values R1 and R2 are determined in advance so that the subject's degree of relaxation can be identified. For example, R1 is set to 10% and R2 is set to 20%. If KJ'>R1, then a relaxation indicator, [C], indicating a low degree of relaxation, is generated. Similarly, if R1≧KJ'>R2, then a relaxation indicator, [B], indicating a moderate degree of relaxation, is generated. When R2≧KJ', then a relaxation indicator, [A], indicating a moderate degree of relaxation, is generated. These indicators may be expressed as message information without further modification, or words or icons may be associated with the indicators. For example, messages such as "regulate breathing, breath more slowly", "concentrate on more relaxed breathing" or "maintain current state" may be displayed in the case of [C], [B], and [A], respectively.

The degree of relaxation during sustained running will now be considered. In this case, the pulse rate is 120 beats/min, and the respiratory rate is 26 times/min (see FIG. 30). If the aforementioned threshold values R1 and R2 are 10% and 20%, respectively, then a respiratory rate of 24~28 times/min would result in a relaxation index of [A], respiratory rates of 21~23 times/min or 28–31 times/min would result in a relaxation index of [B], and respiratory rates of 20 times or less or 32 times or more would result in a relaxation index of [C].

Next, display 17 displays pulse rate information MJ, respiratory rate information KJ, rate-of-change-in-respiratory-rate information KJ', and message information. The subject is thereby made aware of his physiological state, and is able to understand how his degree of relaxation is progressing according to the message displayed. Note that when a rate-of-change-in-respiratory-rate calculating member 15 and a comparing member 16 are not provided to the device main body, the personal computer generates rate-of-change-in-respiratory-rate information KJ' based on relayed respiratory rate information KJ, generates message information, and relays this information to the device main body. In this case, display 17 displays the relayed rate-of-change-in-respiratory-rate information KJ' and message information.

2.3 Operation of Embodiment

Next, the operation of the present embodiment will be explained. The wristwatch and device main body 330 of the personal computer are operated to set the transmission mode to intermittent transmission.

Pulse waveforms are successively detected at the wristwatch via sensor unit 102, and acceleration is detected by the acceleration sensor. The respiratory rate is calculated. The results of the detection and calculation are quantified at a specific sampling frequency, encoded and stored once in controller 109. These results are then displayed on dot display region 108-D as necessary.

Namely, a variety of information can be displayed on dot display region 108-D with button switch 114 employed for the mode setting thereof. Accordingly, when the subject operates button switch 114 to set the operational mode of dot display region 108-D to the "respiratory rate display mode", the respiratory rate is displayed on dot display region 108-D. After data compression has been carried out at specific intervals for the pulse waveform, pulse rate, respiratory rate, and rate of change in respiratory rate recorded in this manner, the data is sent to the personal computer via transmission device 340.

The pulse waveform, pulse rate, respiratory rate and rate of change in respiratory rate sent from the wristwatch are stored in the personal computer, and displayed. These details are monitored by a physician or trainer, and messages are relayed to the subject as necessary. The message may tell the subject to "reduce pace until pulse rate is below 150" or "increase pace until pulse rate is above 50", for example. In this case, the physician or trainer may send messages to the subject after taking into consideration the change rate of the respiratory rate. For example, when the change rate of the respiratory rate is within a fixed range, such that the exercise intensity is deemed appropriate, then a message may be sent telling the subject to "maintain pace". In contrast, when there is a large change rate of the respiratory rate then there is a considerable load on the subject, so that his respiration may become disturbed. Accordingly, in this case, a message may be sent telling the subject to "reduce pace".

Messages may also be relayed according to the current conditions. During a marathon, for example, excitement may cause the rate of change in the subject's respiratory rate to increase significantly when racing against a competitor, even when the subject's lever of exercise is appropriate. In this state, the subject may not make rational decisions, so that energy is wasted and the subject's athletic capabilities are not fully expressed. In this case, it is preferable that the subject calm down so that he is able to perform better. Thus, the trainer is able to detect the subject's degree of relaxation based on the change rate of the respiratory rate and relay a message such as "concentrate on regulating your breathing."

By means of a design for realizing communications between the wristwatch and the personal computer using compressed data in this way, it is possible to decrease the amount of information to be relayed. Communication employing this type of compressed data is equivalent to the case where sending respiratory rate or other information from the personal computer to the wristwatch.

By carrying out specific operations at the wristwatch, it is possible to set upper and lower limit values for the respiratory rate, pulse rate and change rate of the respiratory rate. If the pulse rate, respiratory rate or change rate of the respiratory rate exceed the upper limit value or fall below the lower limit value, then piezo element 120 sounds a warning, and a flashing display of that value (pulse rate, respiratory rate, or rate of change in respiratory rate) is carried out.

Thus, even when a physician or trainer is not available, the subject is able to set the training load so that it is within an appropriate range. Moreover, the subject is made aware of his mental state during exercise, and, by controlling it, can maintain a state of relaxation.

2.4 Effects of Embodiment

In the preceding embodiment, band pass filtering is carried out using a window function on the frequency spectrum of the fingertip plethysmogram envelope, and the body motion spectrum is removed based on the output signal from the acceleration sensor. As a result, it is possible to remove the effects of an arrhythmia, disturbance and voluntary breathing during exercise, so that the respiratory rate can be measured easily and accurately.

Moreover, the hardware employed in the pulse wave measurement can be carried over, so that a special sensor for measuring the respiratory rate is not needed. Thus, the device can be design at a very moderate cost.

3. Embodiment 2

The second embodiment of the present invention will now be explained. The structure and operation of the hardware in the second embodiment are equivalent to those in the first embodiment, with the exception of the following point. Namely, in contrast to the first embodiment, in which the respiratory rate was calculated based on the blood pressure value $y_1$ (fingertip plethysmogram envelope), the invention according to the second embodiment calculates the respiratory rate based on the pulse wave cycle $T_{pulse}$.

First, pulse wave cycle $T_{pulse}$ is recorded over a specific period of time (30 seconds to 1 minute, for example) at waveform extraction recording member 180 of the wristwatch. Since this pulse wave cycle $T_{pulse}$ is discreet along the time axis, a suitable method of interpolation is employed to interpolate the intervals between adjacent $T_{pulse}$, to obtain a curved line (pulse wave cycle envelope) equivalent to that shown in FIG. 9(a). As in the case of the fingertip plethysmogram envelope, this pulse wave cycle envelope also includes LF, HF and trend components. Accordingly, analysis using the same method as in Embodiment 1 is performed, to obtain the respiratory rate and change rate of the respiratory rate.

4. Embodiment 3

In the preceding first and second embodiments, body motion was detected using an acceleration sensor 11. In contrast, in this embodiment, the body motion component is removed without using acceleration sensor 11.

4.1. Overall Structure of Embodiment 3

Figure 23:
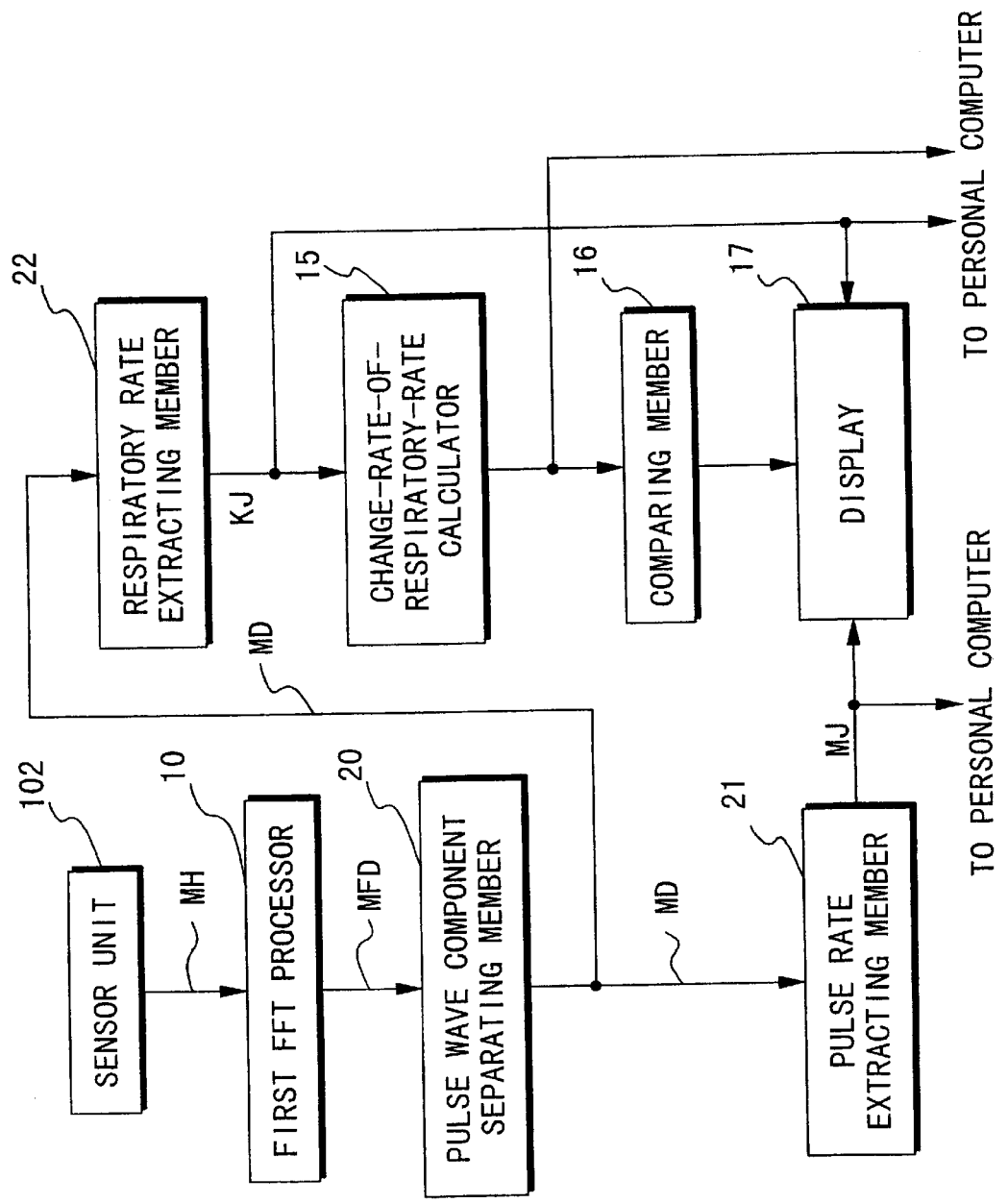
FIG. 23 is a block diagram showing the functional structure of the third embodiment.

The outer design according to the third embodiment of the present invention is equivalent to that of Embodiment 1. The structure of Embodiment 3 will now be explained with reference to the block diagram shown in FIG. 23. Unlike the structure of Embodiment 1 shown in FIG. 21, the structure shown in FIG. 23 is not provided with an acceleration sensor 11 or second FFT processor 12, but is provided with a pulse wave component separating member 20 in place of body motion removing member 13, and a pulse beat extracting member 21 and respiratory rate extracting member 22 in place of a pulse and respiratory rate extracting member 14.

These points of difference will now be explained.

4.2. Pulse Wave Component Separating Member

Pulse wave component separating member 20 is formed of a low pass filter. Pulse wave component separating member 20 removes the pulse wave component from the pulse wave analysis data MFD to generate analysis data MD' from which the pulse wave component has been removed, and to generate pulse wave component analysis data MD. The cut-off frequency of the low pass filter is selected to be slightly lower than the fundamental frequency of the pulse wave component. The reason for this is that the fundamental frequency of the body motion component and the fundamental frequency of the respiratory component are lower then the fundamental frequency of the pulse wave component. More specifically, the cut-off frequency is set to be slightly lower than the fundamental frequency of the pulse wave component measured during rest.

Figure 24:
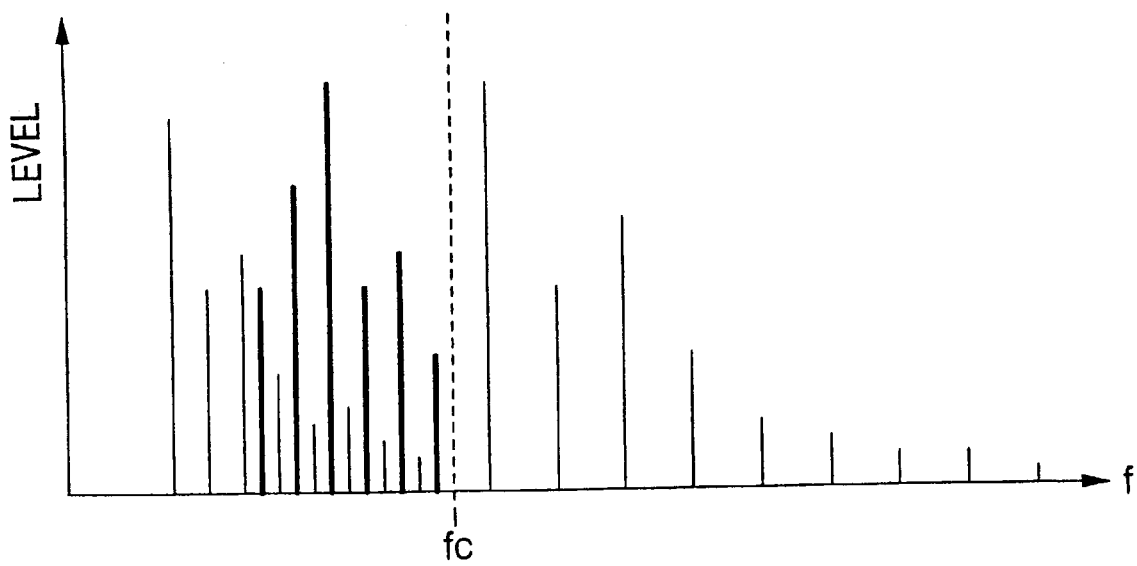
FIG. 24 shows the relationship between pulse wave analysis data MFD and the cut-off frequency fc of the low pass filter.
Figure 25A:
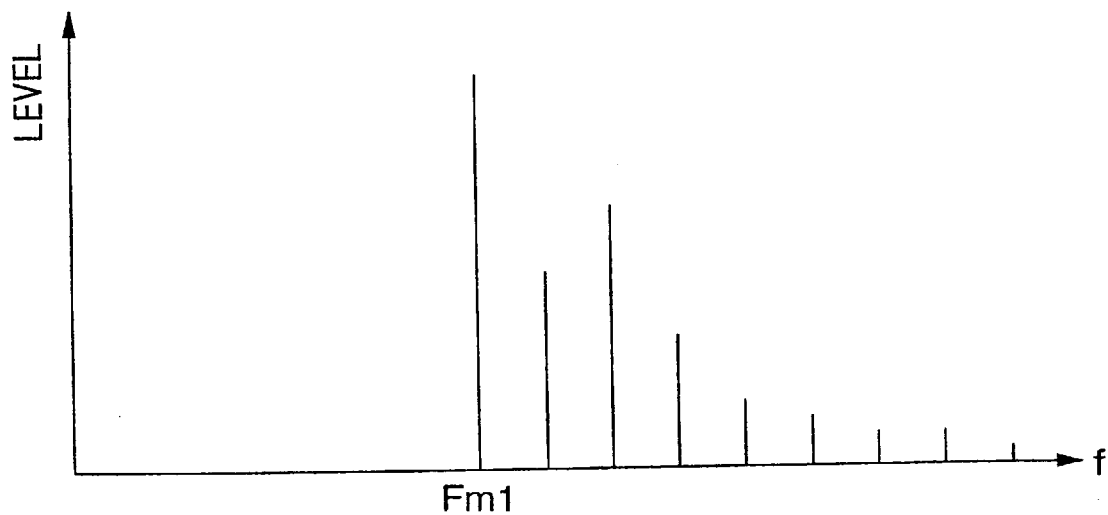
FIG. 25($a$) shows pulse wave component analysis data MD.
Figure 25B:
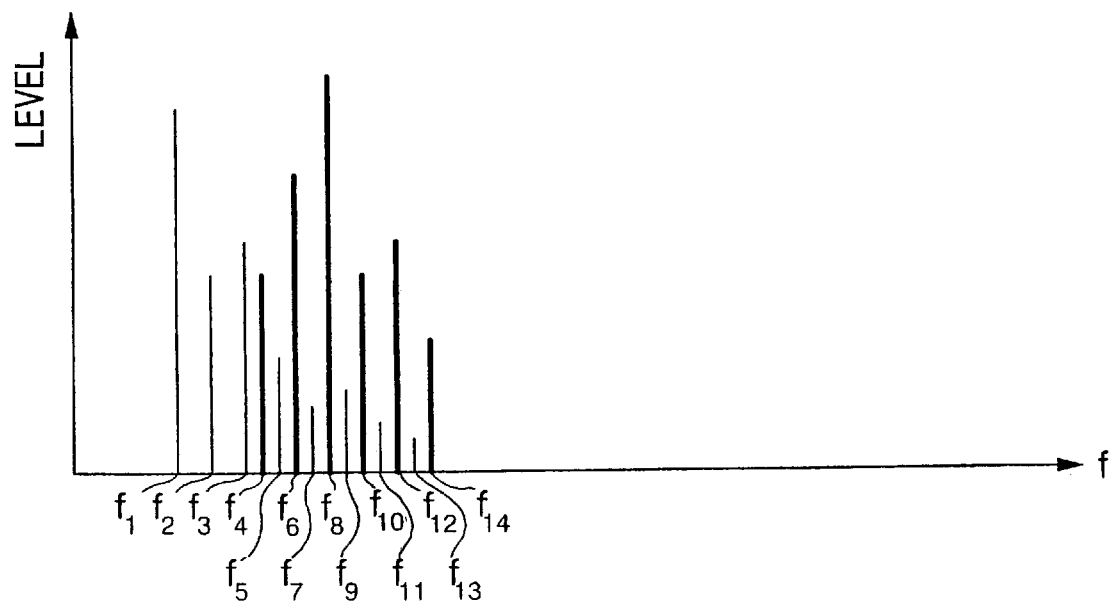

For example, if the pulse wave analysis data MFD and the low pass filter cut-off frequency fc are related as shown in FIG. 24, then the pulse wave component analysis data MD becomes as shown in FIG. 25(*a*) and the analysis data MD' from which the pulse wave component has been removed becomes as shown in FIG. 25(*b*).

4.3. Pulse Rate Extracting Member

Pulse rate extracting member 21 specifies the maximum peak frequency of the pulse wave component analysis data MD as the fundamental frequency Fm1 of the pulse wave component, calculates 60/Fm1, and generates pulse rate information MJ.

4.4. Respiratory Rate Extracting Member

Respiratory rate extracting member 22 generates respiratory rate information KJ from analysis data MD' from which the pulse wave component has been removed. FIG. 26 is a block diagram showing the detailed functional structure of respiratory rate extracting member 22.

In this figure, spectrum extracting member 40 extracts two spectral frequencies as one pair from each spectral frequency of the analysis data MD' from which the pulse wave component has been removed. The lower spectral frequency is output to fundamental frequency table 41, and the higher spectral frequency is output to difference detecting member 42.

For example, if analysis data MD' from which the pulse wave component has been removed is as shown in FIG. 25(*b*), then optional spectral frequencies are extracted as pairs from among spectral frequencies f1~f14. In this case, $_{14}C_2$ is the pair of extracted spectral frequencies. Further, if the spectral frequency pair is f1 and f3, then f1 is output to the fundamental frequency table 41 and f3 is output to the difference detecting member 42.

Next, fundamental frequency table 41 is formed of a ROM or the like, and stores fundamental frequencies Ft1 of the body motion component which have been associated with the fundamental frequency Fm1 of the respiratory component. Fundamental frequency table 41 is formed of actual measured values.

Figure 27:
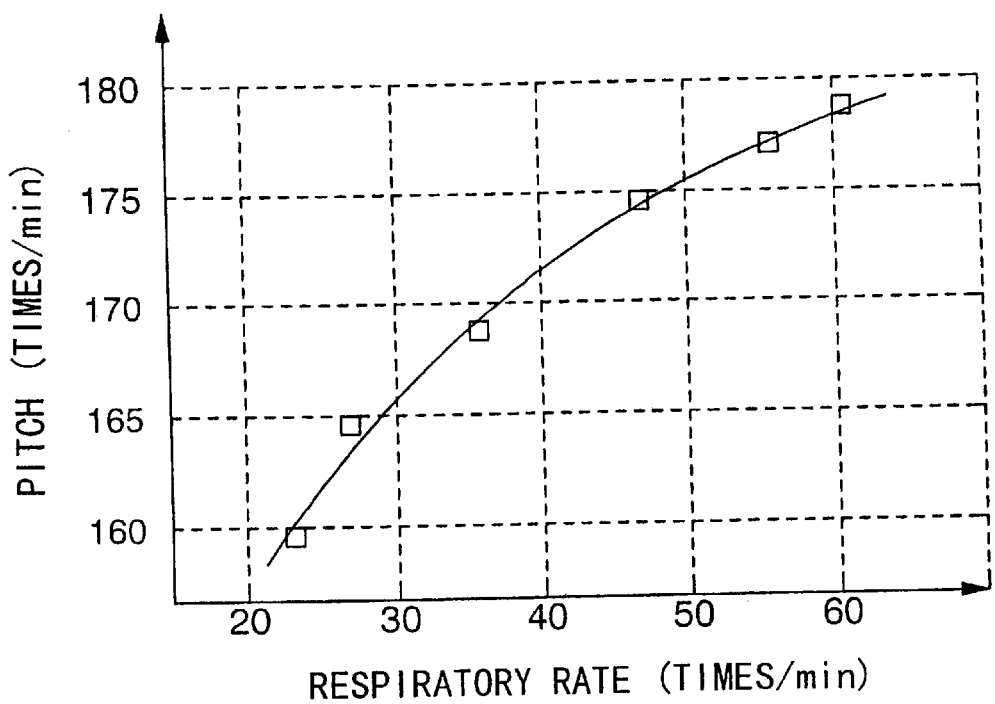
FIG. 27 shows the results of experiments to measure the relationship between running pitch and respiratory rate.

When setting up the data for fundamental frequency table 41, the present inventors had subjects vary running speed in a step-wise manner, and then measured the relationship between running pitch and respiratory rates. FIG. 27 shows the results of these experiments. Running pitch is the number of steps per unit time. In this example, sensor unit 102 is attached to the base of the finger as shown in FIG. 10. The body motion component present in the pulse waveform MH detected as a result is effected by the movement of the arms. The relationship between running pitch and arm movement will differ depending on whether the subject is swinging his arms with great force or not. Typically, however, one swinging rotation of one arm corresponds to 2 running pitches. Further, the cycle for a single arm swing corresponds to one cycle of the body motion waveform. Therefore, if P designates running pitch (times/min), and V designates respiratory rate (times/min), then the fundamental frequency Ft1 of the body motion component and the fundamental frequency Fv1 of the respiratory component can be obtained from the following equation using running pitch P and respiratory rate V.

$$Ft1 = P/(60 \cdot 2) \quad Fv1 = V/60$$

Figure 28:
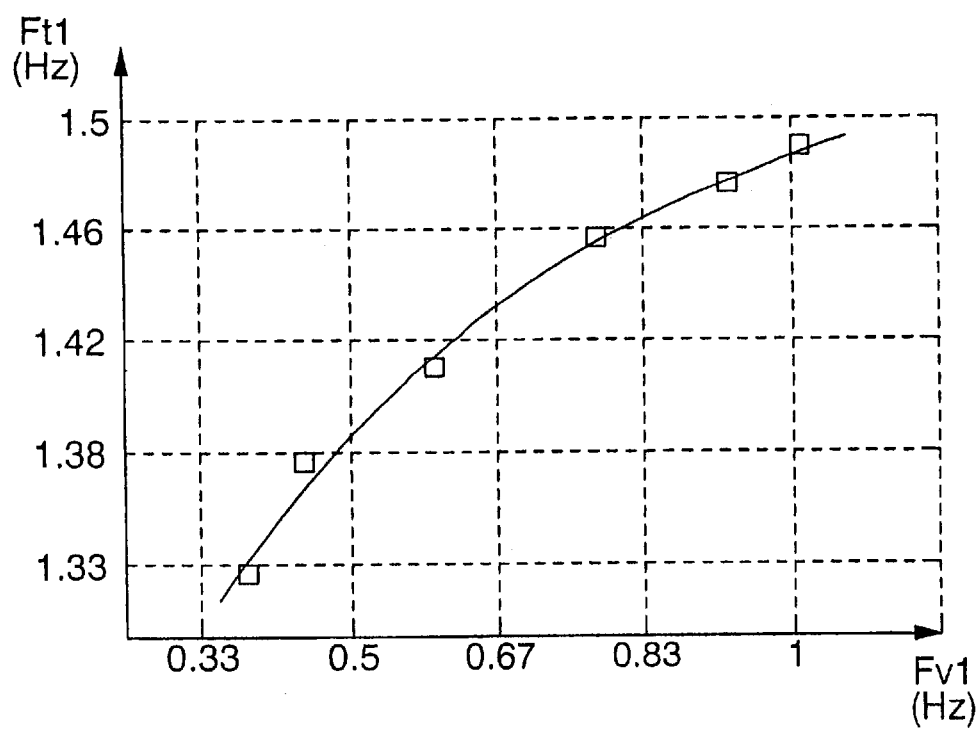
FIG. 28 shows the relationship between the fundamental frequency Ft1 of the body motion component and the fundamental frequency Fv1 of the respiratory rate component.

When the graph shown in FIG. 27 is converted using the above formulas, the relationship between the fundamental frequency Ft1 of the body motion component and the fundamental frequency Fv1 of the respiratory component can be obtained. This relationship is shown in FIG. 28. The data in fundamental frequency table 41 is shown in FIG. 28, for example.

Difference detecting member 42 detects the difference between the frequency output from fundamental frequency table 41 and other spectral frequencies output from spectrum extracting member 40. If the pair of spectral frequencies extracted by spectrum extracting member 40 are fundamental frequency Ft1 of the body motion component and fundamental frequency Fv1 of the respiratory component, then Fv1 is supplied to fundamental frequency table 41 and Ft1 is output. Thus, the output of difference detecting member 42 is [0]. On the other hand, if the pair of spectral frequencies extracted by spectral extracting member 40 is Fv1 and F (where Fv1<F), then the output of difference detecting member 42 becomes [|F−Ft1|]. Therefore, the spectral frequency pair for which the output of difference detecting member 42 becomes the smallest is Ft1 and Fv1.

Next, comparing member 43 compares the output of difference detecting member 42 for each pair of spectral frequencies output from spectral extracting member 40, specifies the pair for which the value is smallest, and outputs the lower of the spectral frequencies making up the pair. In this case, the specified pair is Ft1 and Fv1. Since Ft1>Fv1, the fundamental frequency Fv1 of the respiratory component is output from comparing member 43.

Next, calculating member 44 calculates respiratory rate information KJ by calculating 60/Fv1, based on the fundamental frequency Fv1 of the respiratory component. In this way, the generated respiratory rate information KJ is supplied to rate-of-change-in-respiratory-rate calculating member 15 explained in connection with the first embodiment, to generate rate-of-change-in-respiratory-rate information KJ'.

This embodiment focuses on the relationship between the fundamental frequency Ft1 of the body motion component and the fundamental frequency Fv1 of the respiratory component, and separates the body motion component and the respiratory component at respiratory rate extracting member 22. As a result, respiratory rate information KJ and rate-of-change-in-respiratory-rate information KJ' can be calculated without using an acceleration sensor 11, second FFT processor 12 or the like. As a result, the device can be made smaller and more lightweight, so that the device is easier for the subject to use.

5. Modifications

The present invention is not limited to the embodiments described above, but rather, various modifications such as described below are possible.

(1) The above embodiments employed examples in which a wristwatch was used as the portable device worn by the subject. However, other portable devices are also possible.

Figure 13:
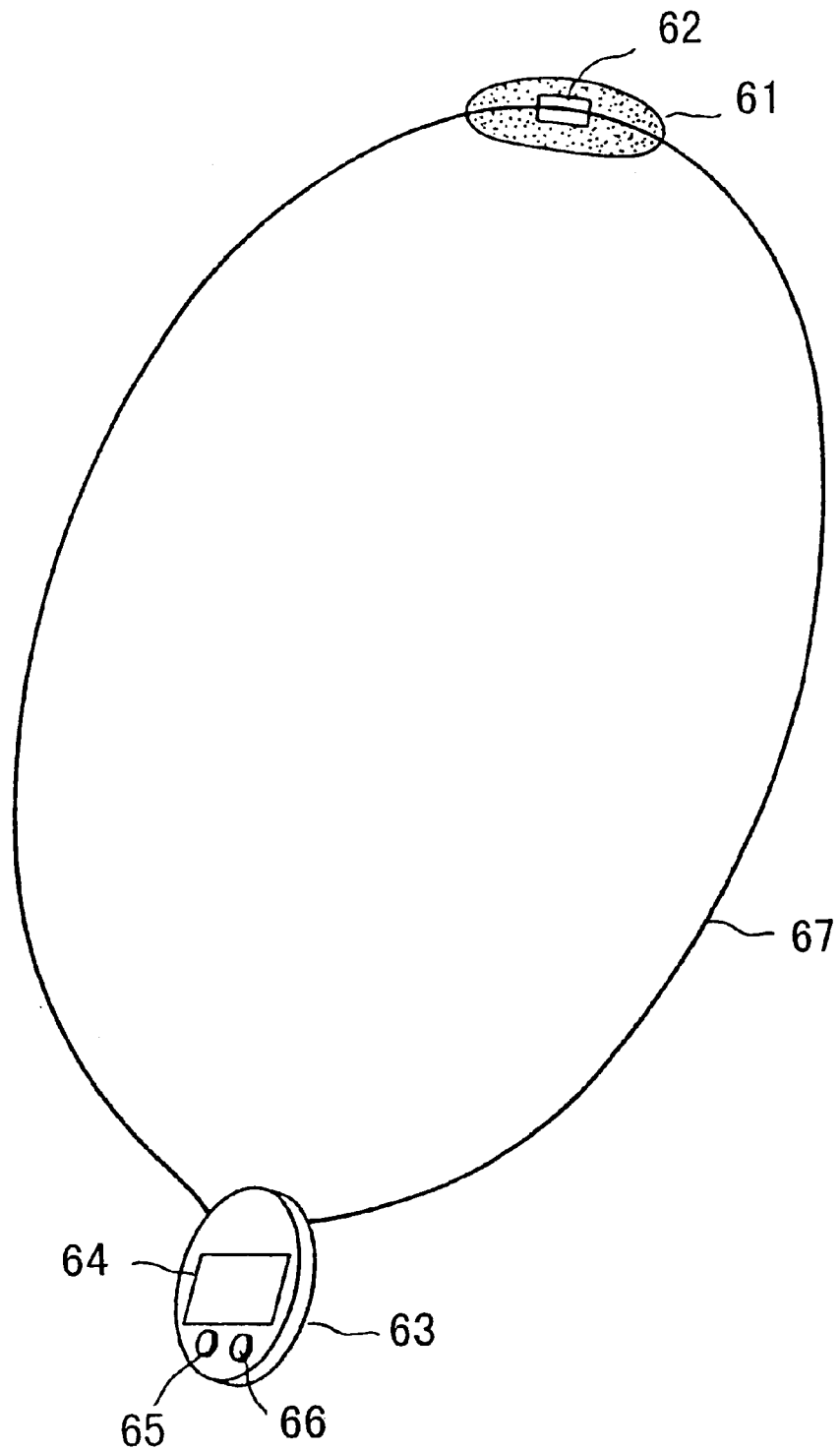
FIG. 13 shows an arrangement in which the photoelectric pulse wave sensor has been incorporated into a necklace.

For example, the photoelectric pulse wave sensor may be combined with an accessory, one example of which is the necklace shown in FIG. 13. In this figure, 61 is a sensor pad, and is comprised, for example, of a shock absorbing material such as a sponge. A photoelectric pulse wave sensor 62 is attached inside sensor pad 61 so as to contact the skin surface. As a result, when the necklace is worn, photoelectric pulse wave sensor 62 comes in contact with the skin at the back of the neck, enabling measurement of the pulse wave.

The main components of the device incorporating the pulse wave detector are incorporated into a hollow main body 63. Main body 63 is a case which is in the form of a broach, the front surface having a graphic display or buttons, for example. The functions of display 64 and buttons 65,66 will differ according to the device into which the pulse wave detector is incorporated.

Photoelectric pulse wave sensor 62 and main body 63 are attached via a chain 67, and are connected electrically via a lead wire (not shown) embedded in chain 67.

(2) Similarly, the photoelectric pulse wave sensor may be combined with a pair of eyeglasses. The display device for notifying the user in this case is also incorporated in the design. Accordingly, in addition to explaining the device's function as a pulse wave detector, its function as a display device will also be explained.

Figure 14:
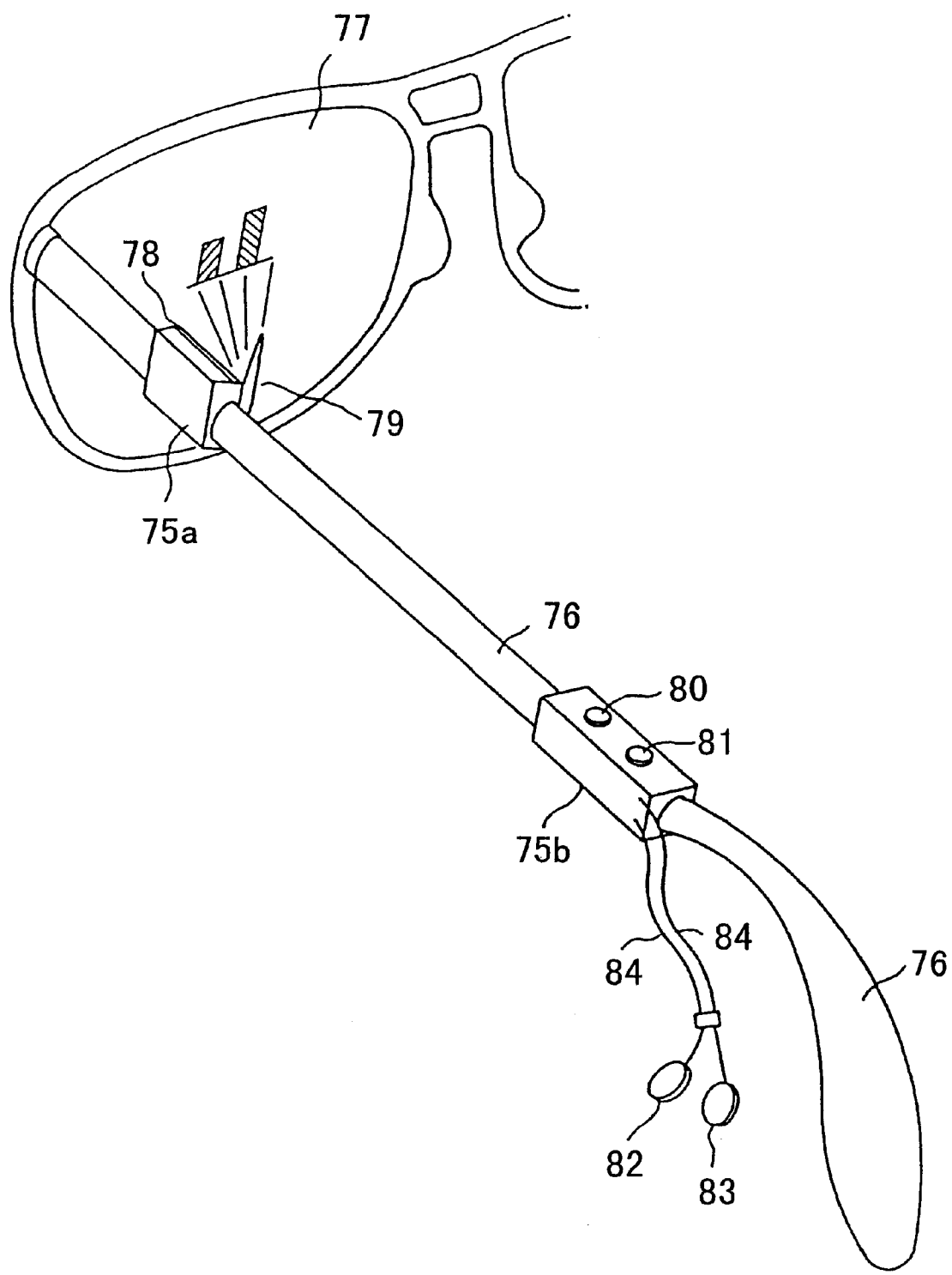
FIG. 14 shows an arrangement in which the photoelectric pulse wave sensor has been combined with a pair of eyeglasses

FIG. 14 is a squint view showing an arrangement in which a device attached to a pulse wave detector is attached to a pair of eyeglasses. As shown in this figure, the device main body is divided into body 75a and body 75b, each of which are attached to the stems 76 of the eyeglasses. Bodies 75a, 75b are electrically attached to one another through a lead wire embedded inside stems 76.

Body 75a houses a display control circuit. A liquid crystal panel 78 is attached over the entire surface of the lens 77 side of case 75a. A mirror 79 is fixed to the edge of this lateral surface at a specific angle. A drive circuit for liquid crystal panel 78 which includes a light source (not shown) and a circuit for forming the display data are incorporated in body 75a. The light emitted from this light source passes via liquid crystal panel 78, and is reflected at mirror 79 to incident on lens 77 of the eyeglasses. The main elements of the device are incorporated in body 75b, and a variety of buttons are provided to the upper surface thereof.

The functions of buttons 80,81 will differ according to the device.

The light emitting diode and optical sensor (see FIG. 3) which form the photoelectric pulse wave sensor are housed in pads 82,83. By clipping the earlobe between pads 82,83, the pulse wave sensor can be fixed in place. Pads 82,83 are electrically connected by lead wires 84,84 which can be pulled out from body 75b.

(3) When employing a wristwatch as the portable device, the site of attachment of sensor unit 102 is not limited to the base of the finger. For example, as shown in FIG. 12, the fingertip plethysmogram may be measured by attaching a sensor unit 102 and sensor fixing pad 104 to the fingertip.

(4) The preceding embodiments employed calculation of the respiratory rate based on the pulse wave as an example of circulatory system information. However, the circulatory system information employed is not limited to the pulse wave. Rather, calculations may be made based on the electrocardiogram for example.

Figure 8:
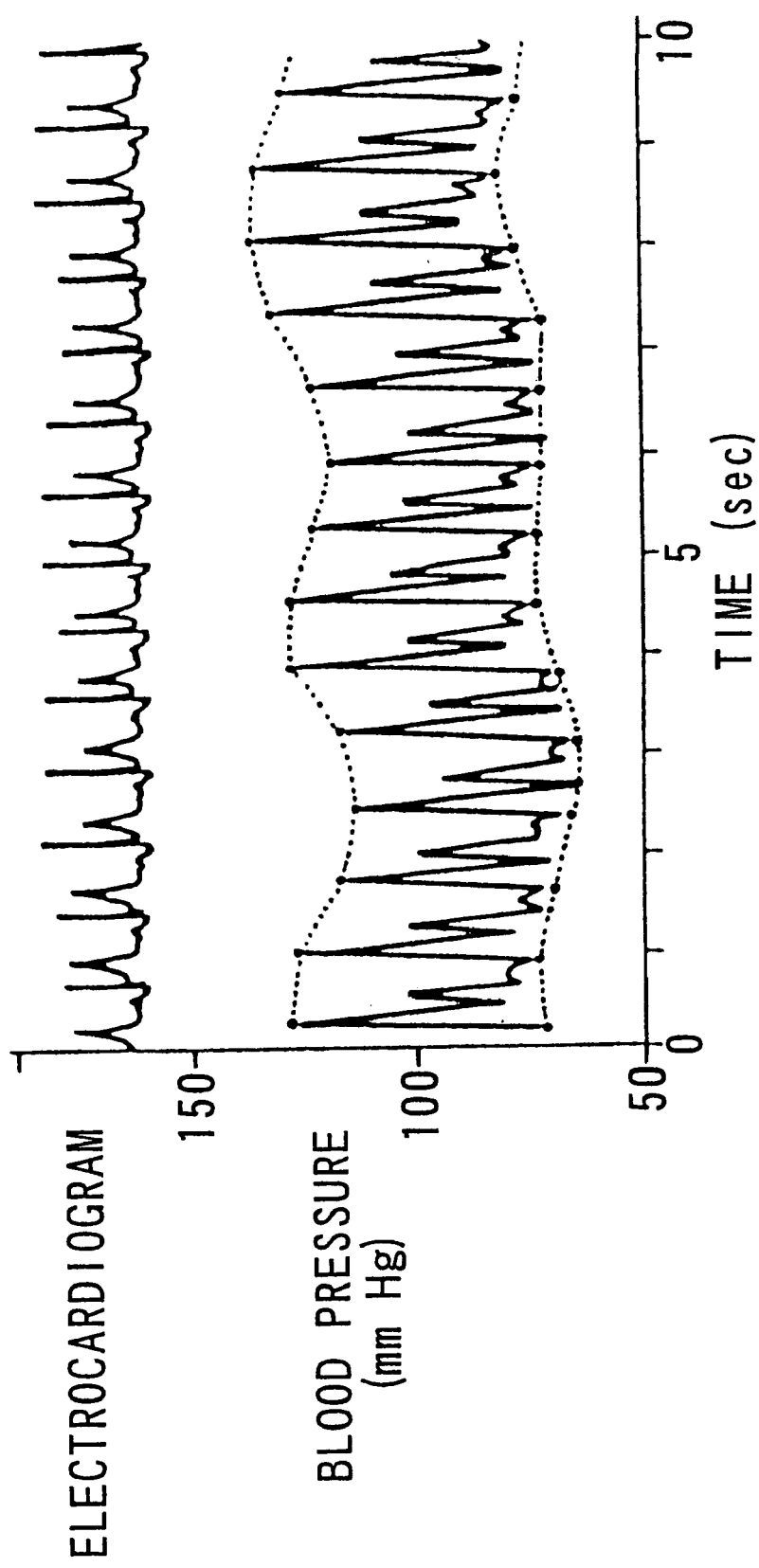
FIG. 8 shows the relationship between the electrocardiogram and the pulse wave.
Figure 9:
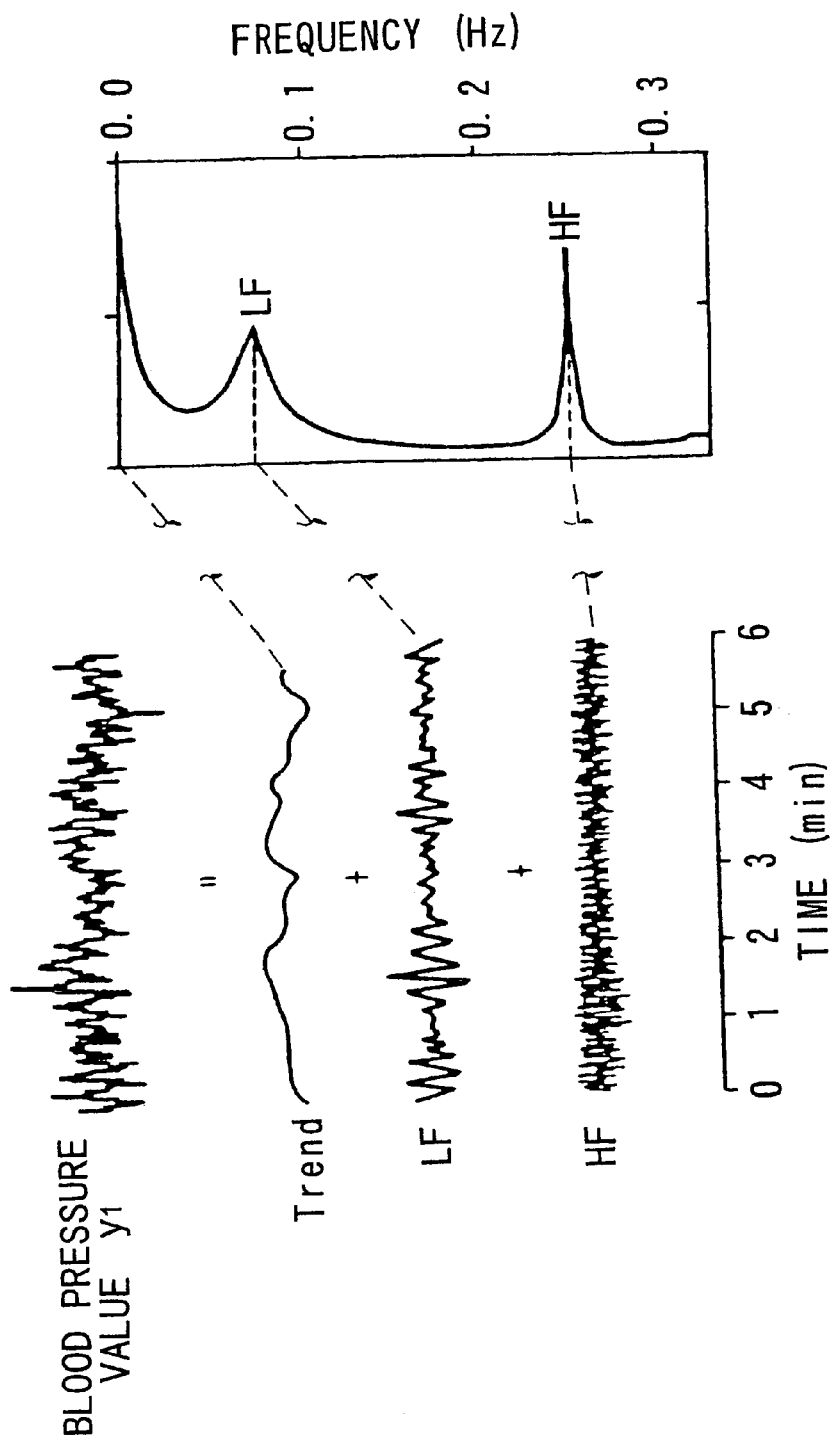
FIGS. 9A and 9B show the fingertip plethysmogram envelope, the components making up the envelope, and the results obtained when spectral analysis is performed on the fingertip plethysmogram envelope.

For example, when an envelope is obtained for the electrocardiogram shown in FIG. 8 that is the same as the enveloped obtained for the pulse wave in the same figure, the respiratory rate can be calculated based on fluctuations in the amplitude values of the level of the electrocardiogram.

Further, if the R—R interval is used in place of the pulse wave cycle $T_{pulse}$, then the respiratory rate can be calculated based on the amount of change in the cycle of the electrocardiogram level. When using the electrocardiogram level in this way, in the case where the subject is exercising, an electromyogram becomes superimposed as a noise component on the electrocardiogram waveform. Accordingly, it is acceptable to remove the electromyogram using the same method as described above.

(5) In the preceding embodiments, the pulse-to-respiratory ratio $\alpha_0$ was set to a value around [4+−0.5], depending on the individual subject. However, it is also acceptable to provide a temperature sensor to measure the subject's body surface temperature, and then adjust the pulse-to-respiratory ratio $\alpha_0$ in response to the body surface temperature. This approach takes into consideration the fact that when the surface body temperature rises, such as when the subject enters a bath, the pulse-to-respiratory ratio $\alpha_0$ increases, even though the subject is in a normal state.

(6) The preceding embodiments employed a piezo element 120 which generated a warning noise, and a liquid crystal display 108 which produced a flashing display, as one example of a warning means. In addition, however, liquid crystal display device 108 can be used to display data such as the respiratory rate and pulse rate to the subject. However, the warning means and display means for the respiratory and pulse rates are not limited to the arrangements described above. Rather, a variety of devices are possible, provided that they carry out a warning which relies on one of the subject's five senses. Accordingly, specific examples of these will be described below.

(6-1) Means Relying on Sense of Hearing

The following are examples of means which rely on the subject's sense of hearing to provide a warning. Many of these can be embedded in a portable device, such as a wristwatch, in which case, the elements incorporated as the watch may be carried over.

(1) buzzer
(2) piezo element
(3) speaker
(4) As a specific example, the subject may be provided with a portable wireless pager by means of which he may be called from the device side when notification Is carried out.

When carrying out notification to a user using this kind of equipment, it is frequently desired to communicate some sort of information along with the notice. In this case, information such as volume levels may be changed as shown below in response to the details of the information to be communicated.

1. pitch
2. volume
3. tone
4. sound
5. type of music (program, etc.)

(6-2) Means Relying on Sense of Sight

A means relying on sight may be employed when the objective is to inform the subject of various measured results or messages from the device, or to provide a warning. For this purpose, the preceding embodiments employed a CRT display 331 or liquid crystal display 108, however a lens projector (see FIG. 14) such as described above may also be used. An X-Y plotter or lamp may also be used.

The following equipment may be considered when providing notification.

Figure 15:
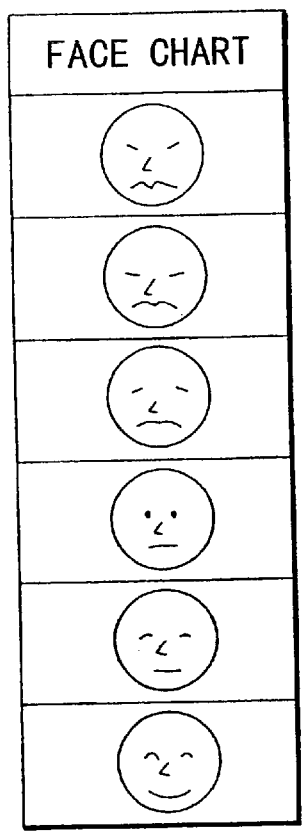
FIG. 15 shows a face chart employed as the notifying means.

1. separate analog or digital displays in the case of notification involving numerical values 2. display using graph
3. addition of contrast to a display color
4. bar graph display where providing notification of a numerical value as in applying a grade to a numerical value
5. circular graph
6. a face chart
7. a flashing display When providing notification by applying a grade to a numerical value such as the respiratory rate, a face chart may be displayed such as shown in FIG. 15 in response to the grade. In this figure, 6 grades are assumed.

(6-3) Means Relying on Tactile Sense

A means relying on tactile sense may also be considered as a warning means. Numerical information such as respiratory and pulse rates can be communicated with a certain degree of accuracy according to the intensity or interval of stimulation. Examples of means for this purpose are as follows.

1. Electrical Stimulation

A form memory alloy projecting outward from the rear surface of a portable device such a wrist watch is provided, with electricity passed through this form memory alloy.

2. Mechanical Stimulation

A retractable projection (such as a needle-shaped object which is not very pointed) may be formed to the rear of a portable device such as a wrist watch, and stimulation may be administered via this projection.

Figure 16:
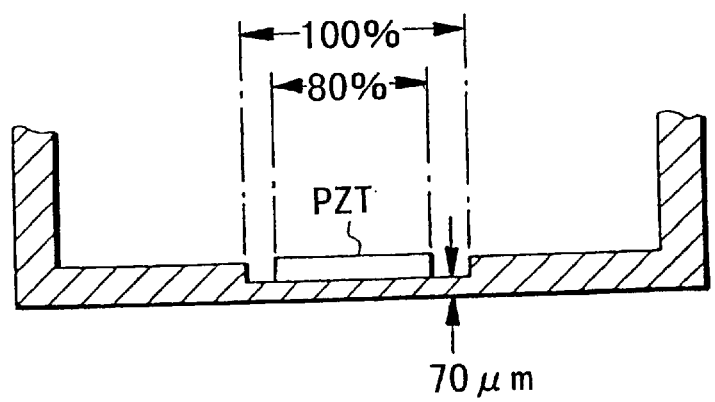
FIG. 16 is a cross-sectional view of the wristwatch in an example in which the notifying means has been incorporated inside the watch, in the case where notification is carried out using a piezo element to create vibration.

Additionally, if the contents of the notification are simple, then the following embodiment may be employed which uses mechanical vibration to notify the user. A conventionally known vibrational alarm which communicates vibration by rotating an eccentric load may be provided in a unitary or separate fashion to the main body of a portable device. Further, as shown in FIG. 16, a thin part of 70 $\mu$m in thickness may be formed to one portion of the inner side of the bottom surface of the main body of a portable device, and a piezoelement PZT attached thereto.

When an alternating current of a suitable frequency is impressed on this piezoelement, the piezoelement PZT vibrates, with this vibration communicated to the user wearing the portable device. Additionally, the piezoelement PZT may have a thickness of 100 $\mu$m, with a diameter length which is 80% of the length of the diameter of the concavity. When the diameter is set to be 80% in this way, it is possible to increase the sound of the notification sound.

By using the preceding mechanisms to change the strength, duration, frequency and the like of the vibration in response to the contents of the notification, it is possible to achieve a notification which is rich in variation.

(6-4) Means Relying on Sense of Smell

A mechanism for emitting a fragrance or the like may be provided to a device as a means relying on the sense of smell. A correspondence can be formed between the notification details and the scent, with the device emitting a fragrance in response to the notification contents. The micropump discussed below is optimally employed for the mechanism for emitting fragrance or the like.

(6-4-1) Micropump Structure

Figure 17:
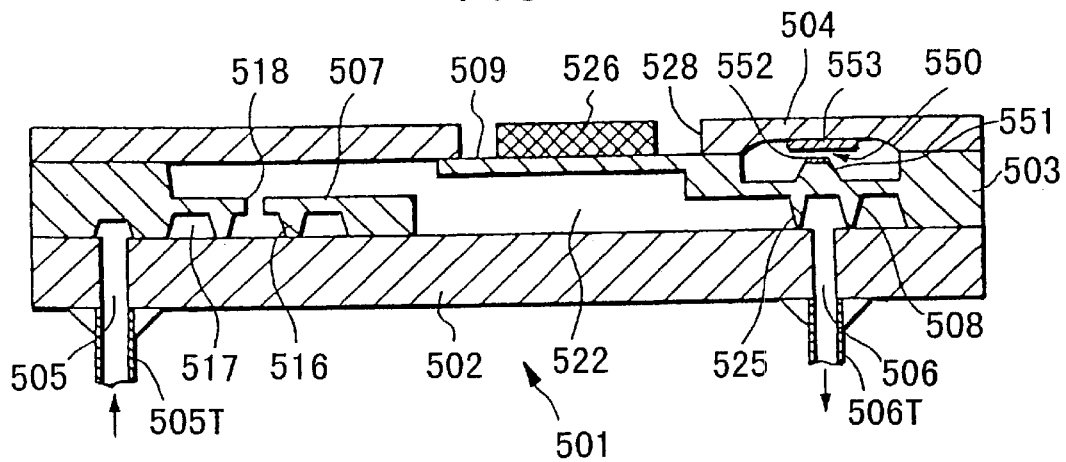
FIG. 17 is a cross-sectional view showing the structure of micropump 501 according to the present invention.

FIG. 17 is a cross-sectional diagram of micropump 501 which has a sandwich structure consisting of base plate 502, thin film 503 and surface plate 504.

Base plate 502 consists of a glass base having a thickness of 1 mm, for example, and is provided with input and output ports 505 and 506, respectively. Tubes 505T and 506T are bonded to these ports by means of an adhesive agent such that there is no leakage therefrom.

Film 503 consists of a Si base having a thickness of 0.3 mm, for example. An entrance valve 507 and an output valve 508, and a diaphragm 509 have been formed to thin film 503 by means of an etching method. A pump chamber 522 and a pump flow system connected thereto are formed below diaphragm 509. A piezo disk type piezo element 526 is bonded to the upper portion of diaphragm 509 as a drive means.

Entrance valve 507 is formed to cover base 502. A communicating hole 518 is formed in the approximate center of the upper surface of entrance valve 507, while a valve 516 is formed projecting downward so as to surround communicating hole 518. The tip of valve 516 extends until base 502. A chamber 517 is formed by the lateral side of entrance valve 507 and valve 516. Chamber 517 connects to input port 505 via a flow system not shown. Output valve 508 is formed of a cap-shaped valve 525 which covers the entrance to output port 506.

Surface plate 504, which consists of the same type of glass plate as base 502, is adhered on to thin film 503 using an anode bonding method. The upper wall of one portion of the flow path of the aforementioned pump flow system is formed by surface plate 504. A window 528 is formed in the spot corresponding to diaphragm 509 on surface plate 504. Piezo element 526 is adhered to the surface of diaphragm 509 which is exposed through window 528. The thickness of surface plate 504 is approximately 1 mm.

Operation detection switch 550 will now be explained. Operation detection switch 550 is provided to detect the behavior of the partition of output valve 508, and consists of projection 551 projecting outward from the top portion of the partition, electrode 552 adhered to the surface of projection 551, and rear electrode 553 which is adhered on the bottom of upper surface plate 504 opposite electrode 552.

As will be explained below, an output pulse from an oscillation circuit 564 is impressed on electrodes 552 and 553 via the condenser C and resistor R shown in FIG. 18. Various interface materials may be employed for electrodes 552 and 553, such as Pt—Ir, W, Ta, Ni, Pt, Pd, Mo, Ti, polycrystal Si, WSi$_2$, CP1, CP2 and the like.

(6-4-2) Structure of the Drive

Figure 18:
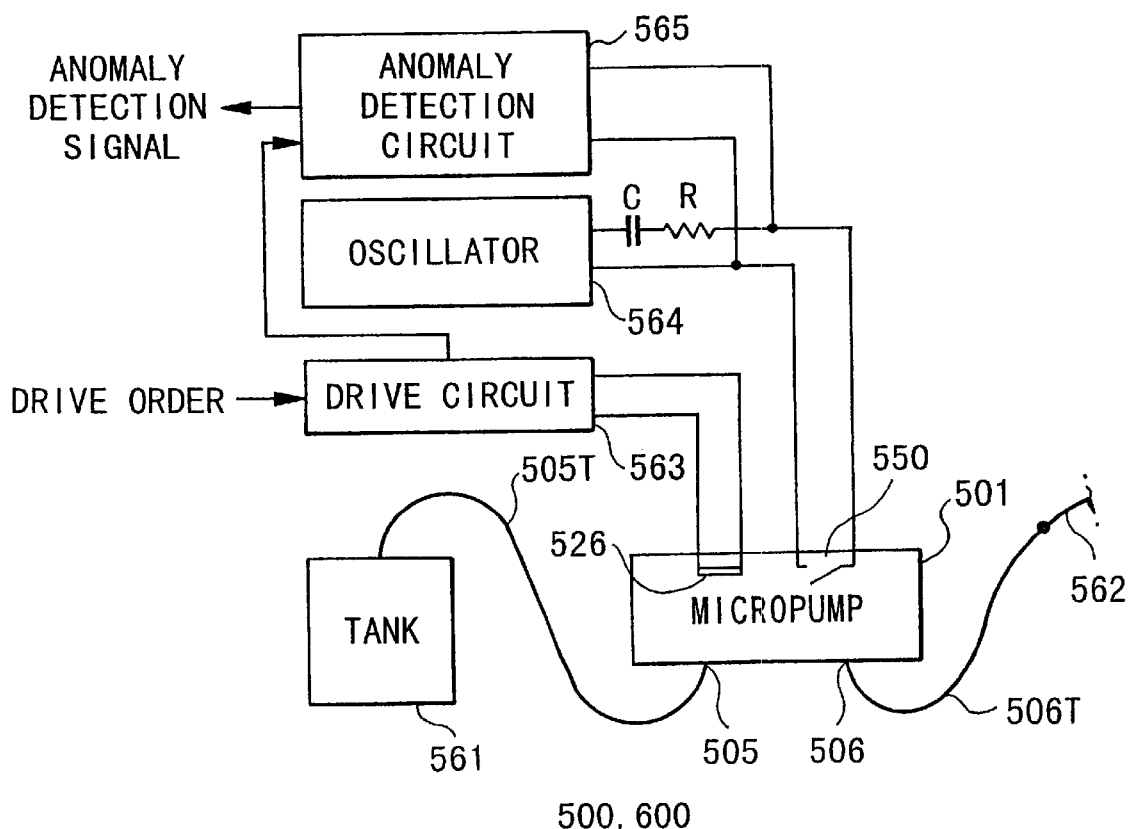
FIG. 18 is a block diagram showing the structure of the driving member for driving micropump 501.

FIG. 18 shows the structure of the drive for driving micropump 501. In this figure, the entire circuit indicated by the numeric symbol 500 (600) forms the drug administrator or fragrance emitter inside the device.

In FIG. 18, 501 is a micropump as explained above. An input port 505 is inserted into a tank 561 via a tube 505T, while output port 506 is connected to tube 506T.

In the case where the device is employed to administer a drug, tube 506T is joined to an injection needle 562 as shown in the figure for that purpose. On the other hand, when the device is employed to emit a fragrance, the tip of tube 506T is instead disposed near a jet opening (explained below) for emitting a fragrance.

When drive circuit 563 receives a drive command from an external device such as a microcomputer, it generates a fixed level (around 100 V) drive pulse which is supplied to piezo element 526, the drive means of micropump 501.

Oscillation circuit 564 generates a plurality of pulses which have cycles which are shorter than the pulse width of the drive pulse. The generated pulses are impressed on operation detection switch 550 of micropump 501 via condenser C and resistor R. Operation detection switch 550 is designed to enter an ON state for a fixed period of time only, each time fluid is expelled from output port 506 of micropump 501. Accordingly, when micropump 501 is operating normally, a drive pulse is impressed on to it, with the pressure at either end of operation detection switch 550 falling each time expulsion of fluid is carried out.

Anomaly detection circuit 565 adjusts the voltage at both ends of operation detection switch 550. When the level of the voltage obtained due to this adjustment does not change over time with respect to the drive pulse, an anomaly detection signal is output. This anomaly detection signal is sent to a microcomputer or the like which controls the micropump.

(6-4-3) Operation of Micropump and Drive

Figure 19:
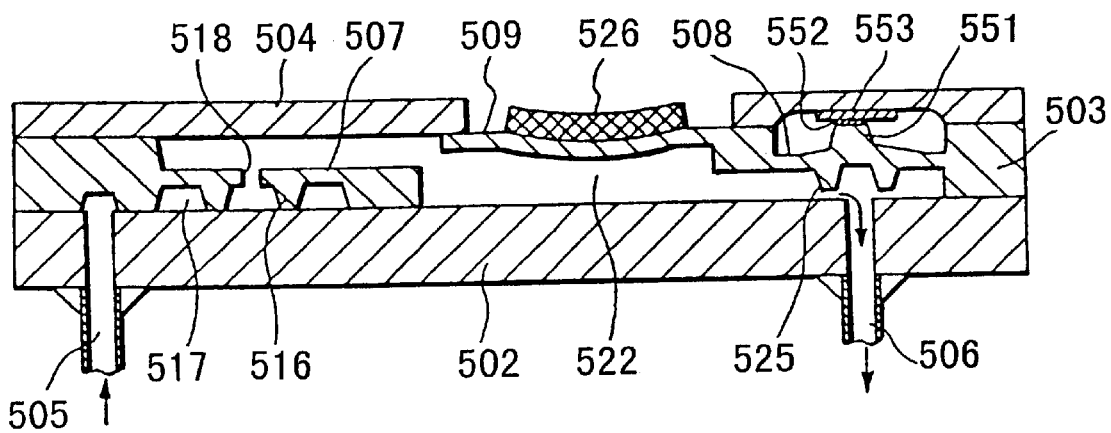
FIG. 19 is an explanatory figure of the operation of micropump 501.

First, drive circuit 563 generates a fixed level (about 100 V) drive pulse when it receives a drive command from a microcomputer or the like provided external to the micropump. The generated drive pulse is supplied to piezo element 526 of micropump 501. When this drive pulse is impressed, piezo element 526 deforms as shown in FIG. 19, bending toward diaphragm 509.

As a result, the pressure inside pump chamber 522 increases, causing the partitioning wall of output valve 508 to be lifted upward and valve 525 to move away from base 502. The fluid (drug, fragrance, etc.) inside pump chamber 522 flows to output port 506 through the opening between valve 525 and base 502, and is emitted via 506T in the case where the device is used to emit a fragrance, or administered via injection needle 562 in the case where the device is employed to administer a drug.

Figure 20:
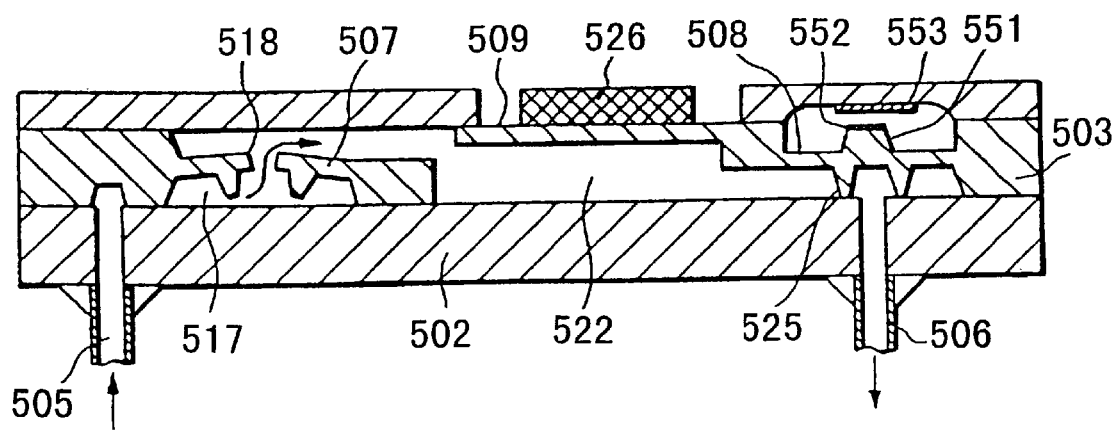
FIG. 20 is an explanatory figure of the operation of micropump 501.

When the drive pulse falls, diaphragm 509 returns to its original shape as shown in FIG. 20, giving rise to a negative pressure in pump chamber 522. As a result, valve 525 of output valve 508 is pressed against base 502, sealing output port 506 as a result. Conversely, when the partitioning wall of input valve 507 is lifted upward, valve 516 moves away from base 502. As a result, fluid flows from input port 505, and is siphoned up into pump chamber 522 via communicating hole 518 and the space between valve 516 and base 502. Thereafter, the expulsion and uptake of the fluid is repeated as above each time a drive pulse is impressed.

During the operation of micropump 501, the voltage at the ends of operation detection switch 550 is monitored by anomaly detection circuit 565. If the fluid is not expelled smoothly due to clogging of the tube or needle, there will be a deviation from the normal relationship between the timing for drive pulse generation and the timing for when operation detection switch 550 enters an ON state. When anomaly detection circuit 565 detects this deviation, an anomaly detection signal is output to the microcomputer, etc.

(7) Frequency analysis of pulse waveform MH and body motion waveform TH was carried out using FFT processing in each of the preceding embodiments. The present invention is not limited thereto, however. Wavelet transformation may also be employed, for example, as may any method which can perform frequency analysis of pulse waveform MH and body motion waveform TH (circulatory state information).

Wavelet transformation may be carried out as follows. In general, in time frequency analysis in which a signal is simultaneously analyzed in both the time and frequency domains, the wavelet forms are the unit by which the signal part is extracted. Wavelet transformation shows the size of the each part of the signal extracted as these units. As the base function for defining wavelet transformation, a function $\psi(x)$ which has been localized with respect to both time and frequency is introduced as the mother wavelet. Here, wavelet transformation employing the mother wavelet $\psi(x)$ of a function f(x) is defined as follows.

$$(W\psi f)(b,a) = \int 1/a^{-\frac{1}{2}} \psi((x-b)/a) f(x) dx$$

In equation (1), b is the parameter employed when translating the mother wavelet $\psi(x)$, while a is the parameter used when scaling. Accordingly, wavelet $\psi((x-b)/a)$ in equation (1) is the wavelet obtained when transitioning mother wavelet $\psi(x)$ by b only, and scaling it by a only. Since the width of the mother wavelet $\psi(x)$ is extended in correspondence to the scale parameter a, 1/a corresponds to the frequency.

Figure 29:
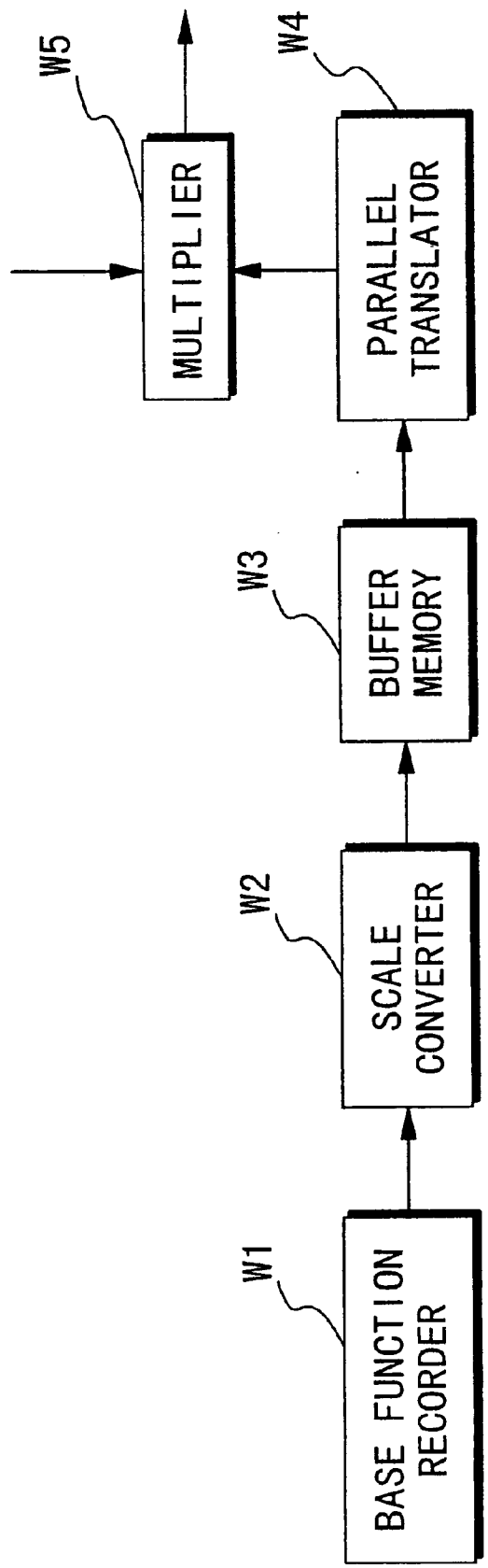
FIG. 29 is a block diagram showing the detailed structure of the wavelet transformer.

A detailed description of wavelet transformation will now be given. FIG. 29 is a block diagram showing the detailed structure of the wavelet transformer. The wavelet transformer is designed to carry out the calculation described by equation 1 above. The wavelet transformer is supplied with clock CK, and carries out calculations according to the clock cycle. As shown in the figure, wavelet transformer 20 consists of a base function recorder W1 which records the mother wavelet $\psi(x)$; a scale converter W2 which converts scale parameter a; buffer memory W3; parallel translator W4 which carries out translation; and multiplier W5. Please note that various types of wavelets may be suitably employed for mother wavelet $\psi(x)$ which is stored in base function recorder W1, including Gabor wavelet, Mexican hat wavelet, Harr wavelet, Meyer wavelet, Shannon wavelet and the like.

When a mother wavelet $\psi(x)$ is read out from base function recorder W1, conversion of scale parameter a is carried out by scale converter W2. Scale parameter a corresponds to period, thus, the bigger a is, the more the mother wavelet extends above the time axis. In this case, the quantity of data for mother wavelet $\psi(x)$ recorded in base function recorder W1 is fixed, so that when a gets larger, the amount of data per unit time decreases. Scale converter W2 carries out interpolation to correct this, and generates a function $\psi(x/a)$ by performing weeding out processing when a gets smaller. This data is stored once in buffer memory W3.

Next, parallel translator W4 reads out function $\psi(x/a)$ from buffer memory W3 at a timing in response to translation parameter b, carrying out the parallel transition of function $\psi(x/a)$, to generate a function $\psi(x-b/a)$.

Next, data which is to undergo wavelet transformation is supplied to multiplier W5. For example, when employing a wavelet transformer as described above in place of first FFT processor 10 shown in FIG. 21, pulse waveform MH is supplied via an A/D converter not shown in the figures. Multiplier W4 carries out wavelet transformation by multiplying variable $1/a^{1/2}$, function $\psi(x-b/a)$ and the pulse waveform MH, to generate pulse wave analysis data MFD. Similarly, a wavelet transformer may also be employed in place of the second FFT processor 12 shown in FIG. 21.

Figure 30:
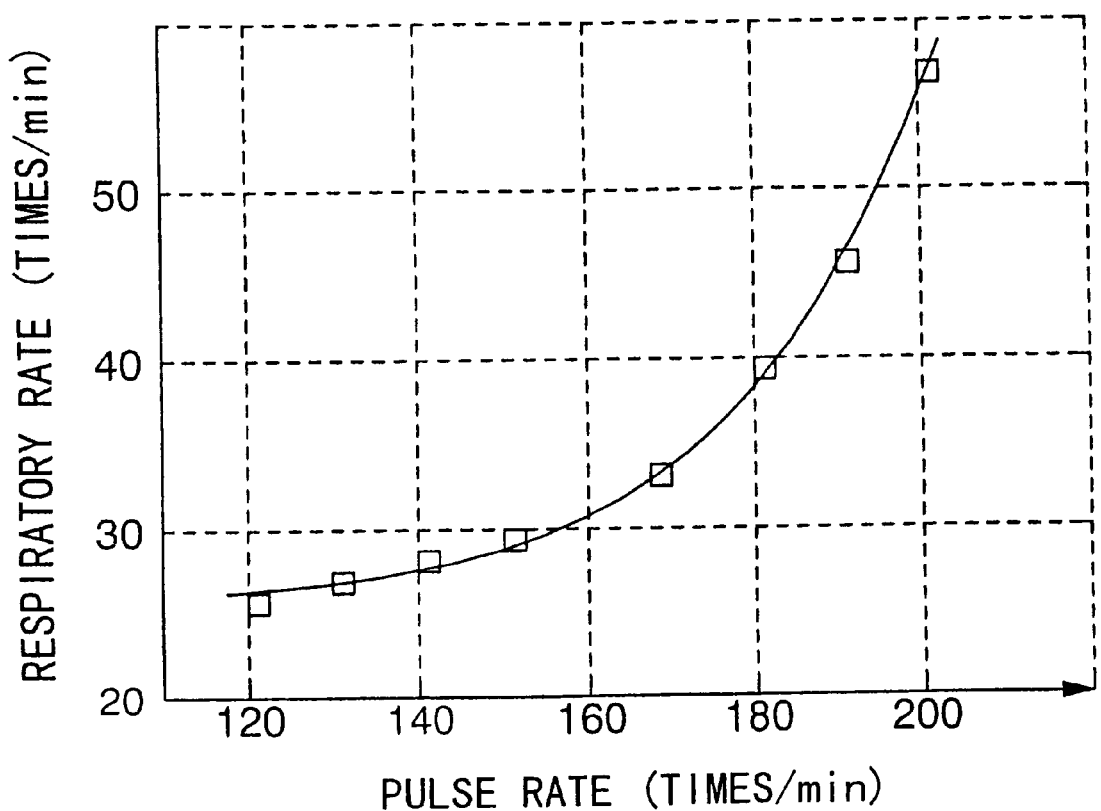
FIG. 30 shows an example of the pulse rate and respiratory rate during running.

(8) Oxygen consumption by skeletal muscle increases as exercise intensity becomes greater. There is a constant relationship between the respiratory and pulse rates. FIG. 30 shows an example of the respiratory and pulse rates during exercise. Filtering may be carried out in Embodiments 1 through 3, according to the connection between the respiratory and pulse rates.

Specifically, a table in which the relationship between respiratory and pulse rates has been stored in advance is provided. The respiratory rate (60/Fv1) is determined by estimating from the pulse rate (60/Fm1) using the table. Using a band pass filter having as the central frequency the fundamental frequency of the estimated respiratory component, the fundamental frequency Fv1 of the respiratory component is extracted. Filtering in this case may be carried out digitally.

As a result, it is possible to even more accurately extract the respiratory component.

(9) In the explanations of the preceding embodiments, threshold values R1 and R2 used in comparing member 16 were fixed. The pulse and respiratory rates are related as shown in FIG. 30. For example, when the acceleration in exercise intensity increases, such as in short- or medium-distance runs, the pulse and respiratory rates increase over a short time period. In this case, even if the runner is running in a relaxed state, the change rate of the respiratory rate increases. Thus, when rate-of-change-in-respiratory-rate information KJ' is compared using fixed threshold value R1,R2, an incorrect degree of relaxation may be detected. Therefore, the threshold values R1,R2 may be varied according to the relationship between the pulse and respiratory rates.

Specifically, a threshold value table in which threshold values R1,R2 dependent on the rate of change in the pulse rate have been stored in advance, and a calculator which calculates rate-of-change-in-pulse-rate information MJ' based on pulse rate information MJ, are provided. Threshold values R1,R2 may then be read out from the threshold table by referencing the rate-of-change-in-pulse-rate information MJ' calculated by the calculator.

As a result, the subject's degree of relaxation can be detected even when the exercise intensity varies dynamically, and an accurate message can be displayed on display 17.

By means of the present invention's physiological state measuring device, the region corresponding to the pulse rate can be extracted from the frequency spectrum of the subject's circulatory state information. Thus, the influence of arrhythmia, distortion, or voluntary breathing during exercise can be removed, so that the respiratory rate can be measured more easily and accurately. Moreover, it is also possible to know the subject's degree of relaxation based on the rate of change in his respiratory rate.

We claim:

1. A physiological state measuring device comprising:
    circulatory system information detecting means for detecting a subject's circulatory system information;
    means for detecting a pulse rate based on the detected circulatory system information;
    means for performing frequency analysis of the detected circulatory system information and for obtaining frequency components;
    determining means for determining a frequency range on the basis of the detected pulse rate;
    limiting means for limiting the obtained frequency components to the frequency range;
    measuring means for measuring a respiratory rate of the subject on the basis of the limited frequency components.

2. A physiological state measuring device according to claim 1, wherein the circulatory system information comprises an amount of change in the cycle of a pulse wave or a level of an electrocardiogram.

3. A physiological state measuring device according to claim 1, wherein the circulatory system information comprises an amount of change in an amplitude value of a pulse wave or a level of an electrocardiogram.

4. A physiological state measuring device according to claim 1, further comprising:
    a portable portion which is worn by the subject for detecting the circulatory system information; and
    a main portion to communicate with the portable portion.

5. A physiological state measuring means according to claim 1, further comprising warning means for providing a warning which relies on one of the subject's five senses, when the measured respiratory rate is outside a specific range.

6. A physiological state measuring device according to claim 1, further comprising communicating means for sending and receiving information including indicators of physiological state to and from an external device which is provided separately from the main body of the device.

7. A physiological state measuring device according to claim 6, wherein the communicating means comprises a recognition information recording means in which particular recognition numbers are provided, wherein a recognition number is associated with communicated information and sent between the external device and the device main body.

8. A physiological state measuring device according to claim 7, wherein data transmission between the device main body and the external device is carried out using compressed data.

9. A physiological state measuring device according to claim 1, further comprising calculating means for calculating the change rate of the respiratory rate based on the measured respiratory rate.

10. The physiological state measuring device, according to claim 9, is used in a relaxation guidance device comprising:
    indicator generating means for generating indicators showing the subject's degree of relaxation based on the change rate of the respiratory rate calculated by the calculating means; and
    notifying means for notifying the subject of the indicator.

11. The physiological state measuring device according to claim 10, wherein the indicator generating means generates an indicator showing the subject's degree of relaxation based on a comparison between a threshold value and the change rate of the respiratory rate.

12. The physiological state measuring device according to claim 11, wherein the indicator generating means comprises:
    pulse rate calculating means for determining pulse rate based on circulatory system information;
    rate-of-change-in-pulse-rate calculating means for calculating the rate of change in the pulse rate; and
    threshold value table for storing in advance threshold values which have been associated with rates of change in the pulse rate;
    wherein, the indicator generating means references the rate of change in the pulse rate calculated by the rate-of-change-in-pulse-rate calculating means, reads out the threshold values from the threshold value table, and generates indicators showing the subject's degree of relaxation based on the threshold value.

13. The physiological state measuring device according to claim 10, further comprising communicating means for sending the change rate of the respiratory rate calculated by the calculating means, and receives the indicator generated by the indicator generating means which is provided to the external device, to and from the external device which is provided external to the main body of the device;
    wherein, the subject is notified of the indicator by the notifying means provided to the device main body.

14. A physiological state measuring device comprising:
    circulatory system information detecting means for detecting information about a subject's circulatory system;
    means for detecting a pulse rate based on the detected circulatory system information;
    means for performing frequency spectral analysis of the detected circulatory system information;
    extracting means for extracting a region determined according to the pulse rate from among the frequency spectrums for the analyzed circulatory system information; and measuring means for measuring the subject's respiratory rate based on the frequency spectrum in the extracted region.

15. A physiological state measuring device according to claim 14, further comprising body motion removing means for removing a body motion spectrum corresponding to the subject's body motion from the frequency spectrum extracted by the extracting means;

wherein, the subject's respiratory rate is generated based on an output from the body motion removing means.

16. A physiological state measuring device according to claim 15, wherein the body motion removing means comprises:

body motion detecting means for detecting the subject's body motion;

body motion spectrum detecting means for determining the body motion spectrum corresponding to the subject's body motion, based on results detected by the body motion detecting means; and body motion correcting means for removing the body motion spectrum from the frequency spectrum extracted by the extracting means.

17. A physiological state measuring device according to claim 15, wherein the body motion removing means comprises:

a fundamental frequency table comprising predetermined associations for the respiratory fundamental frequency and the body motion fundamental frequency according to a change in exercise intensity; and a frequency specifying member for referencing the fundamental frequency table and specifying the respiratory fundamental frequency and the body motion fundamental frequency from among the frequency spectrums extracted by the extracting means;

wherein, the respiratory rate is calculated based on the respiratory fundamental frequency specified by the frequency specifying member.

18. A physiological state measuring means according to claim 16, wherein the body motion detecting means detects acceleration of the subject's arms, and the body motion correcting means removes the body motion spectrum corresponding to the acceleration frequency from the frequency spectrum.

* * * * *

UNITED STATES PATENT AND TRADEMARK OFFICE
CERTIFICATE OF CORRECTION

PATENT NO. : 6,081,742
DATED : June 27, 2000
INVENTOR(S) : Kazuhiko Amano, et al.

It is certified that error appears in the above-identified patent and that said Letters Patent is hereby corrected as shown below:

Title page,
Item [54], please change "organism state measuring device and relaxation instructing device" to -- Physiological state measuring device and relaxation guidance device --.

Item 56, Foreign Patent Documents:
Please change "60-109633 7/1995 Japan" to -- 60-109633 7/1985 Japan --.
Please change "6-227383 8/1995 Japan" to -- 7-227383 8/1995 Japan --.

Signed and Sealed this

Sixteenth Day of October, 2001

Attest:

NICHOLAS P. GODICI
Attesting Officer
Acting Director of the United States Patent and Trademark Office